US008934988B2

United States Patent
Persson et al.

(10) Patent No.: US 8,934,988 B2
(45) Date of Patent: Jan. 13, 2015

(54) ABLATION STENT WITH MEANDER STRUCTURE

(75) Inventors: Torbjorn Persson, Malmo (SE); Cecilia Emanuelsson, Marsta (SE); Hans Abrahamson, Stockholm (SE)

(73) Assignee: St. Jude Medical AB (SE)

( * ) Notice: Subject to any disclaimer, the term of this patent is extended or adjusted under 35 U.S.C. 154(b) by 407 days.

(21) Appl. No.: 13/422,971

(22) Filed: Mar. 16, 2012

(65) Prior Publication Data

US 2013/0245621 A1    Sep. 19, 2013

(51) Int. Cl.
*A61B 18/04* (2006.01)
*A61B 18/14* (2006.01)
*A61F 2/88* (2006.01)
*A61F 2/915* (2013.01)
*A61B 18/00* (2006.01)

(52) U.S. Cl.
CPC ............. *A61B 18/1492* (2013.01); *A61B 18/14* (2013.01); *A61F 2/88* (2013.01); *A61F 2/915* (2013.01); *A61B 2018/00267* (2013.01); *A61B 2018/00404* (2013.01); *A61B 2018/00434* (2013.01); *A61B 2018/00511* (2013.01); *A61B 2018/00577* (2013.01)
USPC ................................ 607/99; 607/101; 606/41

(58) Field of Classification Search
USPC ........................................................ 607/99
See application file for complete search history.

(56) References Cited

U.S. PATENT DOCUMENTS

| 1,384,467 | A | * | 7/1921 | Homan ............................ 607/99 |
| 3,650,277 | A |   | 3/1972 | Sjostrand et al. |
| 4,658,819 | A |   | 4/1987 | Harris et al. |
| 4,886,062 | A | * | 12/1989 | Wiktor ........................... 606/194 |
| 5,035,694 | A |   | 7/1991 | Kasprzyk et al. |
| 5,255,679 | A |   | 10/1993 | Imran |
| 5,300,068 | A |   | 4/1994 | Rosar et al. |
| 5,368,591 | A |   | 11/1994 | Lennox et al. |
| 5,387,233 | A |   | 2/1995 | Alferness et al. |
| 5,421,955 | A | * | 6/1995 | Lau et al. ......................... 216/48 |
| 5,465,717 | A |   | 11/1995 | Imran et al. |
| 5,531,779 | A |   | 7/1996 | Dahl et al. |
| 5,569,295 | A | * | 10/1996 | Lam .............................. 606/198 |
| 5,598,848 | A |   | 2/1997 | Swanson et al. |

(Continued)

FOREIGN PATENT DOCUMENTS

EP          1658818 A1   5/2006
WO          97/45157     12/1997

(Continued)

OTHER PUBLICATIONS

Zazgornik, Jan et al, Bilateral Nephrectomy: The Best, but Often Overlooked, Treatment for Refractory Hypertension in Hemodialysis Patients, AJH 1998; 11:1364-1370.

(Continued)

*Primary Examiner* — Kennedy Schaetzle
(74) *Attorney, Agent, or Firm* — Scott A. Marks

(57) ABSTRACT

Hypertension is treated in a patient by implanting an ablation stent in a renal artery of the patient. Energy is transmitted to the ablation stent to induce heating of the ablation stent, which causes ablation of a renal sympathetic nerve present on the outside of the portion of the renal artery comprising the ablation stent. A preferred ablation stent is in the form of an N-turn coil of an electrically conductive wire forming a meander structure. The respective ends of the wire are electrically connected to each other.

12 Claims, 5 Drawing Sheets

(56) References Cited

U.S. PATENT DOCUMENTS

| | | | |
|---|---|---|---|
| 5,607,462 A | 3/1997 | Imran | |
| 5,628,313 A | 5/1997 | Webster, Jr. | |
| 5,676,662 A | 10/1997 | Fleischhacker et al. | |
| 5,707,400 A | 1/1998 | Terry, Jr. et al. | |
| 5,769,077 A | 6/1998 | Lindegren | |
| 5,772,590 A | 6/1998 | Webster, Jr. | |
| 5,776,161 A * | 7/1998 | Globerman | 606/194 |
| 5,893,885 A | 4/1999 | Webster, Jr. | |
| 5,897,553 A | 4/1999 | Mulier et al. | |
| 5,906,615 A * | 5/1999 | Thompson | 606/45 |
| 5,954,649 A | 9/1999 | Chia et al. | |
| 5,954,719 A | 9/1999 | Chen et al. | |
| 6,004,269 A | 12/1999 | Crowley et al. | |
| 6,012,457 A | 1/2000 | Lesh | |
| 6,016,437 A | 1/2000 | Tu et al. | |
| 6,024,740 A | 2/2000 | Lesh et al. | |
| 6,073,048 A | 6/2000 | Kieval et al. | |
| 6,096,037 A | 8/2000 | Mulier et al. | |
| 6,117,101 A | 9/2000 | Diederich et al. | |
| 6,161,543 A | 12/2000 | Cox et al. | |
| 6,178,349 B1 | 1/2001 | Kieval | |
| 6,200,312 B1 | 3/2001 | Zikorus et al. | |
| 6,216,044 B1 | 4/2001 | Kordis | |
| 6,233,491 B1 | 5/2001 | Kordis et al. | |
| 6,283,951 B1 | 9/2001 | Flaherty et al. | |
| 6,287,608 B1 | 9/2001 | Levin et al. | |
| 6,292,695 B1 | 9/2001 | Webster, Jr. et al. | |
| 6,322,559 B1 | 11/2001 | Daulton et al. | |
| 6,460,545 B2 | 10/2002 | Kordis | |
| 6,522,926 B1 | 2/2003 | Kieval et al. | |
| 6,613,045 B1 | 9/2003 | Laufer et al. | |
| 6,616,624 B1 | 9/2003 | Kieval | |
| 6,632,223 B1 | 10/2003 | Keane | |
| 6,635,054 B2 | 10/2003 | Fjield et al. | |
| 6,656,174 B1 | 12/2003 | Hegde et al. | |
| 6,669,655 B1 | 12/2003 | Acker et al. | |
| 6,699,231 B1 | 3/2004 | Sterman et al. | |
| 6,748,255 B2 | 6/2004 | Fuimaono et al. | |
| 6,805,131 B2 | 10/2004 | Kordis | |
| 6,845,267 B2 | 1/2005 | Harrison et al. | |
| 6,954,977 B2 | 10/2005 | Maguire et al. | |
| 6,970,730 B2 | 11/2005 | Fuimaono et al. | |
| 7,122,031 B2 | 10/2006 | Edwards et al. | |
| 7,149,574 B2 | 12/2006 | Yun et al. | |
| 7,155,284 B1 | 12/2006 | Whitehurst et al. | |
| 7,162,303 B2 | 1/2007 | Levin et al. | |
| 7,209,783 B2 | 4/2007 | Fellows et al. | |
| 7,245,955 B2 | 7/2007 | Rashidi | |
| 7,291,146 B2 | 11/2007 | Steinke et al. | |
| 7,363,076 B2 | 4/2008 | Yun et al. | |
| 7,367,970 B2 * | 5/2008 | Govari et al. | 606/32 |
| 7,419,486 B2 | 9/2008 | Kampa | |
| 7,465,288 B2 | 12/2008 | Dudney et al. | |
| 7,468,062 B2 | 12/2008 | Oral et al. | |
| 7,481,803 B2 | 1/2009 | Kesten et al. | |
| 7,645,409 B2 * | 1/2010 | Saunders et al. | 264/279 |
| 7,653,438 B2 | 1/2010 | Deem et al. | |
| 7,717,948 B2 | 5/2010 | Demarais et al. | |
| 7,742,795 B2 | 6/2010 | Stone et al. | |
| 7,850,685 B2 | 12/2010 | Kunis et al. | |
| 7,949,407 B2 | 5/2011 | Kaplan et al. | |
| 8,145,316 B2 | 3/2012 | Deem et al. | |
| 8,224,416 B2 | 7/2012 | de la Rama et al. | |
| 8,343,213 B2 | 1/2013 | Salahieh et al. | |
| 8,347,891 B2 | 1/2013 | Demarais et al. | |
| 8,442,639 B2 | 5/2013 | Walker et al. | |
| 8,454,594 B2 | 6/2013 | Demarais et al. | |
| 8,545,495 B2 | 10/2013 | Scheib | |
| 2002/0068885 A1 | 6/2002 | Harhen et al. | |
| 2002/0120304 A1 | 8/2002 | Mest | |
| 2003/0050681 A1 | 3/2003 | Pianca et al. | |
| 2003/0055491 A1 * | 3/2003 | Schwartz et al. | 623/1.21 |
| 2003/0060858 A1 | 3/2003 | Kieval et al. | |
| 2003/0074039 A1 | 4/2003 | Puskas | |
| 2003/0114739 A1 | 6/2003 | Fuimaono et al. | |
| 2003/0216792 A1 | 11/2003 | Levin et al. | |
| 2003/0233099 A1 | 12/2003 | Danaek et al. | |
| 2004/0215186 A1 | 10/2004 | Cornelius et al. | |
| 2004/0215310 A1 * | 10/2004 | Amirana | 623/1.11 |
| 2005/0288730 A1 | 12/2005 | Deem et al. | |
| 2006/0030913 A1 | 2/2006 | Eggers et al. | |
| 2006/0089678 A1 | 4/2006 | Shalev | |
| 2006/0248698 A1 * | 11/2006 | Hanson et al. | 29/282 |
| 2007/0135875 A1 | 6/2007 | Demarais et al. | |
| 2008/0033524 A1 * | 2/2008 | Gale | 623/1.11 |
| 2008/0147173 A1 * | 6/2008 | Mciff et al. | 623/1.34 |
| 2008/0255478 A1 | 10/2008 | Burdette | |
| 2009/0076409 A1 | 3/2009 | Wu et al. | |
| 2009/0143777 A1 | 6/2009 | Pacey et al. | |
| 2009/0254164 A1 | 10/2009 | Johnson et al. | |
| 2010/0016762 A1 | 1/2010 | Thapliyal et al. | |
| 2010/0094209 A1 | 4/2010 | Drasler et al. | |
| 2010/0168737 A1 | 7/2010 | Grunewald | |
| 2010/0249773 A1 | 9/2010 | Clark et al. | |
| 2010/0268307 A1 | 10/2010 | Demarais et al. | |
| 2010/0286684 A1 | 11/2010 | Hata et al. | |
| 2011/0004087 A1 | 1/2011 | Fish et al. | |
| 2011/0004290 A1 | 1/2011 | Bales, Jr. et al. | |
| 2011/0118726 A1 | 5/2011 | de la Rama et al. | |
| 2011/0137298 A1 | 6/2011 | Nguyen et al. | |
| 2011/0160720 A1 | 6/2011 | Johnson | |
| 2011/0213231 A1 | 9/2011 | Hall et al. | |
| 2011/0257641 A1 | 10/2011 | Hastings et al. | |
| 2011/0264011 A1 | 10/2011 | Wu et al. | |
| 2011/0264086 A1 | 10/2011 | Ingle | |
| 2012/0143097 A1 | 6/2012 | Pike, Jr. | |
| 2012/0143298 A1 | 6/2012 | Just et al. | |
| 2012/0296232 A1 | 11/2012 | Ng | |
| 2012/0323233 A1 | 12/2012 | Maguire et al. | |
| 2013/0116737 A1 | 5/2013 | Edwards et al. | |
| 2013/0131743 A1 | 5/2013 | Yamasaki et al. | |
| 2013/0144251 A1 | 6/2013 | Sobotka | |
| 2013/0172715 A1 | 7/2013 | Just et al. | |

FOREIGN PATENT DOCUMENTS

| | | |
|---|---|---|
| WO | 00/66020 | 11/2000 |
| WO | 01/00273 | 1/2001 |
| WO | 01/22897 | 4/2001 |
| WO | 02/26314 | 4/2002 |
| WO | 03/082080 | 10/2003 |
| WO | 2006/041881 | 4/2006 |
| WO | 2007/149970 | 12/2007 |
| WO | 2008/141150 | 11/2008 |
| WO | 2008/151001 | 12/2008 |
| WO | 2012/064818 | 5/2012 |
| WO | 2012/106492 | 8/2012 |

OTHER PUBLICATIONS

Robbins, Ivan M. et al, Pulmonary Vein Stenosis After Catheter Ablation of Atrial Fibrillation, Circulation Journal of the American Heart Association, 1998;98:1769-1775.

Rocha-Singh, Krishna J., Catheter-Based Sympathetic Renal Denervation a Novel Strategy for the Treatment of Resistant Hypertension, Endovascular Today, Aug. 2009, 52-56.

Rocha-Singh, Krishna J., Renal Artery Denervation: A Brave New Frontier, Endovascular Today, Feb. 2012, 45-53.

Sanderson, John E. et al, Effect of B-Blockade on Baroreceptor and Autonomic Function in Heart Failure, Clinical Science (1999) 96, 137-146.

Santos, Mario et al, Renal Sympathetic Denervation in Resistant Hypertension, World J Cardiol Apr. 26, 2013; 5(4): 94-101.

Savard, Sebastien et al, Eligibility for Renal Denervation in Patients With Resistant Hypertension When Enthusiasm Meets Reality in Real-Life Patients, J Am Coll Cardiol. 2012;60(23):2422-2424.

Schauerte, Patrick et al, Catheter Ablation of Cardiac Autonomic Nerves for Prevention of Vagal Atrial Fibrillation, Circulation Journal of The American Heart Association, 2000, 102:2774-2780.

(56) References Cited

OTHER PUBLICATIONS

Schlaich, Markus P. et al, International Expert Consensus Statement: Percutaneous Transluminal Renal Denervation for the Treatment of Resistant Hypertension, Journal of the American College of Cardiology vol. 62, Issue 22, Dec. 3, 2013, pp. 2031-2045.
Schlaich, Markus P. et al, Renal Denervation as a Therapeutic Approach for Hypertension Novel Implications for an Old Concept, Hypertension Journal of The American Heart Association, 2009;54:1195-1201.
Schlaich, Markus P. et al, Renal Sympathetic-Nerve Ablation for Uncontrolled Hypertension, The New England Journal of Medicine, 2009; 361:932-934.
Schmieder, Roland E. et al, ESH Position Paper: Renal Denervation—An Iterventional Therapy of Resistant Hypertension, Journal of Hypertension, 2012, 30:837-841.
Schmieder, Roland E. et al, Updated EHS Position Paper on Interventional Therapy of Resistant Hypertension, EuroIntervention 2013; 9:R58-R66.
Sellers, Alfred M. et al, Adrenalectomy and Sympathectomy for Hypertension Ten Year Survival, Archives of Surgery, vol. 89, Nov. 1964, 880-886.
Sen, S.K., Some Observations on Decapsulation and Denervation of the Kidney, The British Journal of Urology, vol. 8, Issue 4, Dec. 1936, 319-328.
Shiraki, Iwao William, Correction of Renal Hypertension by Ligation of Stenotic Segmental Renal Artery, Urology, vol. IX, No. 3, Mar. 1977, 296-298.
Shonai, Takaharu et al, Renal Artery Aneurysm: Evaluation with Color Doppler Ultrasonography Before and After Percutaneous Transarterial Embolization, J Ultrasound Med 19:277-280, 2000.
Silver, Donald et al, Renovascular Hypertension From Renal Artery Compression by Congenital Bands, Annals of Surgery, Feb. 1976, 161-166.
Smith, Gardner W. et al, Surgical Results and the Diagnostic Evaluation of Renovascular Hypertension, Annals of Surgery, May 1968, 669-680.
Smith, Harold P. et al, Radiofrequency Neurolysis in a Clinical Model Neuropathological Correlation, J Neurosurg 55:246-253, 1981.
Smithwick, R.H., An Evaluation of the Surgical Treatment of Hypertension, The Bulletin, Nov. 1949; 25(11):698-716.
Smithwick, Reginald H. et al, Splanchnicectomy for Essential Hypertension, The Journal of the American Medical Association, vol. 152, No. 16, Aug. 1953, 1501-1504.
Solis-Herruzo, J.A. et al, Effects of Lumbar Sympathetic Block on Kidney Function in Cirrhotic Patients with Hepatorenal Syndrome, Journal of Hepatology, 1987; 5: 167-173.
Sowers, James R. et al, Diabetes, Hypertension, and Cardiovascular Disease: An Update, Hypertension Journal of The American Heart Association, 2001;37:1053-1059.
Stanley, James C., Surgical Treatment of Renovascular Hypertension, The American Journal of Surgery, vol. 174, Aug. 1997, 102-110.
Stella, Andrea et al, Effects of Reversible Renal Denervation on Haemodynamic and Excretory Functions of the Ipsilateral and Contralateral Kidney in the Cat, Journal of Hypertension 1986, 4: 181-188.
Stuart, Candace, Newest Frontier in Cardiac Care: Kidneys; Cardiovascular Business, Dec. 13, 2012.
Stuart, Mary, Masterminds of Ardian: An Interview With Inventors Mark Gelfand and Howard Levin, Windhover Information, Start-Up Jan. 1, 2011.
Sun, Yingxian et al, Risk of Coronary Stenosis with Venous Ablation for Epicardial Accessory Pathways, PACE, Apr. 2001, Part II, vol. 24, 605.
Swartz, John F. et al, Radiofrequency Endocardial Catheter Ablation of Accessory Atrioventricular Pathway Atrial Insertion Sites, Circulation Journal of The American Heart Association, 1993;87:487-499.
Teigen, Corey L. et al, Segmental Renal Artery Embolization for Treatment of Pediatric Renovascular Hypertension, Journal of Vascular and Interventional Radiology, 1992; 3:111-117.
Teixeira, Maria Do Carmo et al,1992; Role of the Peripheral Renin Profile in Predicting Blood Pressure Control After Bilateral Nephrectomy in Renal-Transplanted Patients, Nephrol Dial Transplant (1998) 13: 2092-2097.
Teo, W S et al, Radiofrequency Catheter Ablation of Accessory Pathways: The Initial Experience in Singapore, Singapore Medical Journal, 1994; vol. 35:36-40.
Thiebot, J. et al, Bilateral Nephrectomy by Embolization of the Renal Arteries: A Report on Five Cases (author's transl), Sem Hop. Apr. 8-15, 1980;56(13-14):670-5.
Thomas, George et al, Renal Denervation to Treat Resistant Hypertension: Guarded Optimism, Cleveland Clinic Journal of Medicine, vol. 79, No. 7, Jul. 2012, 501-510.
Thomas, Natalie A., Secondary Consideration in Nonobviousness Analysis: The Use of Objective Indicia Following KSR V. Teleflex, NYU Law Review, vol. 86, No. 6, Dec. 2011, 2070-2112.
Ting, Chih-Tai et al, Arterial Hemodynamics in Human Hypertension Effects of Angiotensin Converting Enzyme Inhibition, Hypertension Journal of the American Heart Association, 1993;22:839-846.
Uchida, Fumiya et al, Effect of Radiofrequency Catheter Ablation on Parasympathetic Denervation: A Comparison of Three Different Ablation Sites, PACE, vol. 21, Nov. 1998, Part II, 2517-2521.
Valente, John F. et al, Laparoscopic Renal Denervation for Intractable ADPKD-Related Pain, Nephrol Dial Transplant (2001) 16:160.
Villarreal, Daniel et al, Effects of Renal Denervation on Postprandial Sodium Excretion in Experimental Heart Failure, American Journal of Physiology, May 1994;266(5 Pt 2):R1599-R1604.
Vonend, Oliver et al, Secondary Rise in Blood Pressure After Renal Denervation, The Lancet, vol. 380, Issue 9843, p. 778, Aug. 25, 2012.
Vujaskovic, Z. et al, Effects of Intraoperative Hyperthermia on Canine Sciatic Nerve: Histopathologic and Morphometric Studies, Int. J. Hyperthermia, 1994, Vol. 10, No. 6, 845-855.
Webb, R.L. et al, Functional Identification of the Central Projections of Afferent Renal Nerves, Clin. and Exper.—Theory and Practice, Ag(Suppl.I), 47-57 (1987).
Weinstock, Marta et al, Renal Denervation Prevents Sodium Retention and Hypertension in Salt-Sensitive Rabbits with Genetic Baroreflex Impairment, Clinical Science (1996) 90, 287-293.
Wilcox, Josiah N., Scientific Basis Behind Renal Denervation for the Control of Hypertension, Medtronic, Inc., Dec. 2012, 38 pages.
Winternitz, Sherry R. et al, Role of the Renal Sympathetic Nerves in the Development and Maintenance of Hypertension in the Spontaneously Hypertensive Rat, Journal of Clinical Investigation, vol. 66 Nov. 1980, 971-978.
Wolf-Maier, Katharina et al, Hypertension Treatment and Control in Five European Countries, Canada, and the United States, Hypertension. 2004;43:10-17.
Wyss, J.M. et al, Sensory Denervation of the Kidney Attenuates Renovascular Hypertension in the Rat, Am J Physiol Heart Circ Physiol 250:H82-H86, 1986.
Yamada, Yutaka et al, Age-Related Changes in Muscle Sympathetic Nerve Activity in Essential Hypertension, Hypertension Journal of The American Heart Association, 1989;13:870-877.
Young, Robert R. et al, Reversible Block of Nerve Conduction by Ultrasound Ultrasonic Blocking of Nerve Fibers, Arch Neurol. 1961;4(1):83-89.
Goldberg, S. Nahum MD et al., "Transluminal Radiofrequency Tissue Ablation with Use of Metallic Stents," Journal of Vascular and Interventional Radiology. Sep.-Oct. 1997;8(5):835-843.
Krum, Henry et al., "Catheter-based renal sympathetic denervation for resistant hypertension: a multicentre safety and proof-of-concept study," Lancet 2009;373:1275-1281.
Schwarzwalder, Uwe et al., "Renal Artery Stenting—Developments in Practice," Interventional Cardiology. 2009;4:104-108.
Schlaich, Markus P. MD et al., Renal Sympathetic-Nerve Ablation for Controlled Hypertension, N Eng J Med. 2009;361(9):932-934.
Abboud, Francois M., The Sympathetic System in Hypertension, State-of-the-Art Review, Hypertension Journal of the American Heart Association, Hypertension 4 (suppl II): II-208-II-225, 1982.
Allen, Edgar V., Sympathectomy for Essential Hypertension, Circulation Journal of the American Heart Association, vol. VI, Jul. 1952, 131-140.

(56) References Cited

OTHER PUBLICATIONS

Anderson, Erling A. et al, Elevated Sympathetic Nerve Activity in Borderline Hypertensive Humans, Evidence From Direct Intraneural Recordings, Hypertension Journal of the American Heart Association, vol. 14, No. 2, Aug. 1989, 177-183.
Ardian, Inc., Ardian(R) Receives 2010 EuroPCR Innovation Award and Demonstrates Further Durability of Renal Denervation Treatment for Hypertension, PR Newswire, Jun. 3, 2010.
Arentz, Thomas et al, Feasibility and Safety of Pulmonary Vein Isolation Using a New Mapping and Navigation System in Patients with Refractory Atrial Fibrillation, Circulation Journal of the American Heart Association, Nov. 18, 2003, 2484-2490.
Badoer, Emilio et al, Cardiac Afferents Play the Dominant Role in Renal Nerve Inhibition Elicited by Volume Expansion in the Rabbit, American Journal of Physiology, 1998, R383-R388.
Bakris, George L. et al, Baroreflex Activation Therapy Provides Durable Benefit in Patients with Resistant Hypertension: Results of Long-Term Follow-up in the Rheos Pivotal Trial, J Am Soc Hypertens. Mar.-Apr. 2012;6 (2):152-8.
Bao, Gang et al, Blood Pressure Response to Chronic Episodic Hypoxia: Role of the Sympathetic Nervous System, American Journal of Physiology, 1997, 95-101.
Barajas, Luciano et al, Anatomy of the Renal Innervation: Intrarenal Aspects and Ganglia of Origin, Canadian Journal of Physiology and Pharmacology, vol. 70, No. 5, May 1992, 735-749.
Barajas, Luciano et al, Monoaminergic Innervation of the Rat Kidney: A Quantitative Study, American Journal of Physiology, vol. 259, No. 3, Sep. 1990, F503-F511.
Bardram, Linda et al, Late Results After Surgical Treatment of Renovascular Hypertension, A Follow-up Study of 122 Patients 2-18 Years After Surgery, Annals of Surgery, vol. 201, No. 2, Feb. 1985, 219-224.
Bello-Reuss, Elsa et al, Effect of Renal Sympathetic Nerve Stimulation on Proximal Water and Sodium Reabsorption, The Journal of Clinical Investigation, vol. 57, Apr. 1976, 1104-1107.
Bello-Reuss, Elsa et al, Effects of Acute Unilateral Renal Denervation in the Rat, The Journal of Clinical Investigation, vol. 56, Jul. 1975, 208-217.
Benito, Fernando et al, Radiofrequency Catheter Ablation of Accessory Pathways in Infants, Heart, 1997, 78, 160-162.
Bernardi, Luciano et al, Influence of Type of Surgery on the Occurrence of Parasympathetic Reinnervation After Cardiac Transplantation, Circulation Journal of The American Heart Association, Apr. 14, 1998;97(14):1368-74.
Bertog, Stefan C. et al, Renal Denervation for Hypertension, JACC: Cardiovascular Interventions, vol. 5, No. 3, Mar. 2012, 249-258.
Bertram, Harald et al, Coronary Artery Stenosis After Radiofrequency Catheter Ablation of Accessory Atrioventricular Pathways in Children with Ebstein's Malformation, Circulation Journal of the American Heart Association, 2001, 538-543.
Blankestijn, Peter J. et al, Renal Denervation: Potential Impact on Hypertension in Kidney Disease?, Nephrol Dial Transplant (2011) 0: 1-3.
Blankestijn, Peter J. et al, Sympathetic Overactivity in Renal Failure Controlled by ACE Inhibition: Clinical Significance, Nephrol Dial Transplant, 2000, 15, 755-758.
Blum, Ulrich et al, Treatment of Ostial Renal-Artery Stenoses with Vascular Endoprostheses After Unsuccessful Balloon Angioplasty, The New England Journal of Medicine, vol. 336, No. 7, Feb. 1997, 459-465.
Brinkmann, Julia et al, Catheter-Based Renal Nerve Ablation and Centrally Generated Sympathetic Activity in Difficult-to-Control Hypertensive Patients Prospective Case Series, Hypertension. 2012;60:1485-1490.
Brookes, Linda et al, Renal Denervation: Is Reality Meeting Expectations?, An Interview with Michel Azizi, MD, PhD, Medscape, Jan. 7, 2013.
Bunte, Matthew C. et al, Endovascular Treatment of Resistant and Uncontrolled Hypertension, JACC: Cardiovascular Interventions, vol. 6, No. 1, 2013, 1-9.

Calleary, Hickey D. et al, Pre-Transplant Bilateral Native Nephrectomy for Medically Refractory Hypertension, The Irish Medical Journal, Jul.-Aug. 2001;94(7):214-6.
Callens, David J. et al, Narrowing of the Superior Vena Cava-Right Atrium Junction During Radiofrequency Catheter Ablation for Inappropriate Sinus Tachycardia: Analysis with Intracardiac Echocardiography, Journal of the American College of Cardiology, vol. 33, No. 6, 1999, 1667-1670.
Campese, V.M., Is Hypertension in Chronic Renal Failure Neurogenic in Nature?, Nephrol Dial Transplant, 1994, 9: 741-742.
Campese, Vito M. et al, Neurogenic Factors in Renal Hypertension, Current Hypertension Reports, 2002 4: 256-260.
Campese, Vito M. et al, Renal Afferent Denervation Prevents Hypertension in Rats With Chronic Renal Failure, Hypertension, 1995, 25, 878-882.
Campese, Vito M. et al, Renal Afferent Denervation Prevents the Progression of Renal Disease in the Renal Ablation Model of Chronic Renal Failure in Rat, American Journal of Kidney Disease, vol. 26, No. 5, Nov. 1995, 861-865.
Campese, Vito M., Interventional Hypertension: A New Hope or a New Hype? The Need to Redefine Resistant Hypertension, J Hypertens. Nov. 2013;31(11):2118-21.
Canadian Agency for Drugs and Technologies in Health, Catheter-Based Renal Denervation for Treatment-Resistant Hypertension; Issues in Emerging Health Technologies, Issue 121, Mar. 2013.
Carlstedt, Thomas et al, Regrowth of Lesioned Dorsal Root Nerve Fibers into the Spinal Cord of Neonatal Rats, Neuroscience Letters Feb. 10, 1987;74(1)14-8.
Chabanier, H. et al, On the Decapsulation and Neurectomy of the Kidnesy in Permanent Hypertensive States, The Medical Press, Feb. 22, 1936, No. 16, 307-310.
Ciccone, C D et al, Effects of Acute Renal Denervation on Kidney Function in Deoxycorticosterone Acetate-Hypertensive Swine, Hypertension Journal of the American Heart Association, Oct. 1986, vol. 8, No. 10, 925-931.
Ciriello, John et al, Renal Afferents and Hypertension, Current Hypertension Reports 2002, 4:136-142.
Converse, Richard L. et al, Sympathetic Overactivity in Patients with Chronic Renal Failure, The New England Journal of Medicine, vol. 327, No. 27, 1992, 1912-1918.
Crile, George, The Clinical Results of Celiac Ganglionectomy in the Treatment of Essential Hypertension, Annals of Surgery, Jun. 1938; 107(6): 909-916.
Cruickshank, J.M., Beta-Blockers Continue to Surprise Us, European Heart Journal (2000) 21, 354-364.
Curtis, John J. et al, Surgical Therapy for Persistent Hypertension After Renal Transplantation, Transplantation, vol. 31, No. 2, 1981, 125-128.
Dailey, U.G., Surgical Treatment of Hypertension: A Review-Part II, Journal of the National Medical Association, May 1948, vol. 40, No. 3., 113-116.
Dailey, U.G., Surgical Treatment of Hypertension: A Review-Part III, Journal of the National Medical Association, Jul. 1948, vol. 40, No. 4, 160-162.
Dailey, U.G., The Surgical Treatment of Hypertension: A Review, Journal of the National Medical Association, Mar. 1948, vol. 40, No. 2, 76-79.
Davis, Mark I. et al, Effectiveness of Renal Denervation Therapy for Resistant Hypertension A Systematic Review and Meta-Analysis, Journal of the American College of Cardiology, vol. 62, No. 3, 2013, 231-241.
De Wardener, H.E., The Hypothalamus and Hypertension, Physiological Reviews, vol. 81, No. 4, Oct. 2001.
Dequattro V. et al, The Sympathetic Nervous System: The Muse of Primary Hypertension, Journal of Human Hypertension, 2002, 16 (Suppl 1), S64-S69.
Dibona, Gerald F. et al, Neural Control of Renal Function, Physiological Reviews, vol. 77, No. 1, Jan. 1997, 75-197.
Dibona, Gerald F. et al, Translational Medicine: The Antihypertensive Effect of Renal Denervation, Americal Journal of Physiology, 2010, 298, R245-R253.

(56) References Cited

OTHER PUBLICATIONS

Dibona, Gerald F., Neural Control of Renal Function: Cardiovascular Implications, Hypertension Journal of The American Heart Association, vol. 13, No. 6, Part 1, Jun. 1989, 539-548.

Dibona, Gerald F., Neural Control of the Kidney: Functionally Specific Renal Sympathetic Nerve Fibers, American Journal of Physiology, 2000, 279, R1517-R1524.

Dibona, Gerald F., Neural Control of the Kidney: Past, Present, and Future, Hypertension Journal of The American Heart Association, vol. 41, Mar. 2003, Part II, 621-624.

Dibona, Gerald F., Renal Innervation and Denervation: Lessons from Renal Transplantation Reconsidered, Artificial Organs, vol. 11, No. 6, 1987, 457-462.

Dibona, Gerald F., Role of the Renal Nerves in Renal Sodium Retention and Edema Formation, Trans Am Clin Climatol Assoc. 1990; 101: 38-45.

Dibona, Gerald F., Sympathetic Nervous System and Hypertension, Hypertension Journal of The American Heart Association, 2013; 61: 556-560.

Dibona, Gerald F., Sympathetic Nervous System and the Kidney in Hypertension, Curr Opin Nephrol Hypertens. Mar. 2002;11(2):197-200.

Dibona, Gerald F., The Sympathetic Nervous System and Hypertension, Hypertension Journal of The American Heart Association, Vo. 43, Feb. 2004, 147-150.

Doumas, Michael et al, Interventional Management of Resistant Hypertension, The Lancet, vol. 373, Apr. 11, 2009, pp. 1228-1230.

Dubuc, Marc et al, Feasibility of Cardiac Cryoablation Using a Transvenous Steerable Electrode Catheter, Journal of Interventional Cardiac Electrophysiology, 1998, 2: 285-292.

Elmula, Fadl et al, Renal Sympathetic Denervation in Patients With Treatment-Resistant Hypertension After Witnessed Intake of Medication Before Qualifying Ambulatory Blood Pressure, Hypertension. 2013;62:526-532.

Esler, M. et al, Sympathetic Nerve Activity and Neurotransmitter Release in Humans: Translation from Pathophysiology into Clinical Practice, Scandinavian Physiological Society, 2003, 177, 275-284.

Esler, Murray D. et al, Renal Sympathetic Denervation in Patients with Treatment-Resistant Hypertension (The Symplicity HTN-2 Trial): A Randomised Controlled Trial, Lancet, 2010; 376:1903-1909.

Esler, Murray et al, Assessment of Human Sympathetic Nervous System Activity from Measurements of Norepinephrine Turnover, Hypertension Journal of The American Heart Association, vol. 11, No. 1, Jan. 1988, 3-20.

Evelyn, Kenneth A. et al, Effect of Thoracolumbar Sympathectomy on the Clinical Course of Primary (Essential) Hypertension, American Journal of Medicine, Feb. 1960, 188-221.

Freyberg, R. H. et al, The Effect on the Kidney of Bilateral Splanchnicectomy in Patients with Hypertension, The Journal of Clinical Investigation, vol. 16, Issue 1, Jan. 1937, 49-65.

Gafoor, Sameer et al, Nonresponders to Renal Denervation for Resistant Hypertension, Endovascular Today, Oct. 2013, 63-70.

Garel, L. et al, Fatal Outcome After Ethanol Renal Ablation in Child with End-Stage Kidneys; AJR 146:593-594, Mar. 1986.

Gazdar, A. F. et al, Neural Degeneration and Regeneration in Human Renal Transplants, The New England Journal of Medicine, vol. 238, No. 5, Jul. 1970, 222-224.

Goldberg, Michael R. et al, Reconstructive Vascular Surgery for Renovascular Hypertension, Can Med Assoc J. Feb. 2, 1974;110(3):275-80.

Golwyn, Daniel H. et al, Percutaneous Transcatheter Renal Ablation with Absolute Ethanol for Uncontrolled Hypertension or Nephrotic Syndrome: Results in 11 Patients with End-Stage Renal Disease, Journal of Vascular and Interventional Radiology, Jul.-Aug. 1997, vol. 8, No. 4, 527-533.

Gorisch, Wolfram et al, Heat-Induced Contraction of Blood Vessels, Lasers in Surgery and Medicine 2:1-13 (1982).

Grassi, Guido et al, Baroreflex Control of Sympathetic Nerve Activity in Essential and Secondary Hypertension, Hypertension Journal of The American Heart Association, 1998;31:68-72.

Grassi, Guido et al, Dissociation Between Muscle and Skin Sympathetic Nerve Activity in Essential Hypertension, Obesity, and Congestive Heart Failure, Hypertension. 1998;31:64-67.

Grimson, Keith S. et al, Results of Treatment of Patients with Hypertension by Total Thoracic and Partial to Total Lumbar Sympathectomy, Splanchnicectomy and Celiac Ganglionectomy, Annals of Surgery, Jun. 1949, vol. 129, No. 6, 850-871.

Grimson, Keith S. et al, Total Thoracic and Partial to Total Lumbar Sympathectomy, Splanchnicectomy and Celiac Ganglionectomy for Hypertension, Annals of Surgery, Oct. 1953, vol. 138, No. 4, 532-547.

Grimson, Keith S., Total Thoracic and Partial to Total Lumbar Sympathectomy and Celiac Ganglionectomy in the Treatment of Hypertension, Annals of Surgery, Oct. 1941, vol. 114, No. 4, 753-775.

Guyton, Arthur C., Blood Pressure Control Special Role of the Kidneys and Body Fluids, Science, vol. 252, Jun. 1991, 1813-1816.

Hafkenschiel, Joseph H. et al, Primary Hypertension Survey of the Survival of Patients with Established Diastolic Hypertension After Ten Years of Medical and Surgical Treatment, The American Journal of Cardiology, vol. 16, Jul. 1965, 61-66.

Hafkenschiel, Joseph H. et al, The Surgical Treatment of Hypertension with Particular Reference to Andrenalectomy and Sympathectomy, Transactions. American College of Cardiology, vol. 5, Dec. 1955, pp. 107-112.

Hall, J.E. et al, Role of Sympathetic Nervous System and Neuropeptides in Obesity Hypertension, Brazilian Journal of Medical and Biological Research, 2000, 33:605-618.

Hall, John E., The Kidney, Hypertension, and Obesity, Hypertension. 2003;41:625-633.

Hall, Winthrop H. et al, Combined Embolization and Percutaneous Radiofrequency Ablation of a Solid Renal Tumor, American Journal of Roentgenology, 174, Jun. 2000, 1592-1594.

Hamm, Christian et al, Confluence, Issue eight, Apr. 2014.

Han, Young-Min et al, Renal Artery Embolization with Diluted Hot Contrast Medium: An Experimental Study, Journal of Vascular and Interventional Radiology, Jul. 2001;12(7):862-868.

Hansen, Jesper Melchoir et al, The Transplanted Human Kidney Does Not Achieve Functional Reinnervation, Clinical Science, (1994) 87, 13-20.

Heuer, George J., The Surgical Treatment of Essential Hypertension, Annals of Surgery, Oct. 1936, vol. 104, No. 3, 771-786.

Hinton, J. William, End Results of Thoracolumbar Sympathectomy for Advanced Essential Hypertension, The Bulletin, Apr. 1948, 239-252.

Holmer, Stephan et al, Role of Renal Nerves for the Expression of Renin in Adult Rat Kidney, The American Journal of Physiology, May 1994;266(5 Pt 2):F738-F745.

Hoobler, S.W. et al, The Effects of Splanchnicectomy on the Blood Pressure in Hypertension, Circulation Journal of The American Heart Association, vol. IV, Aug. 1951, 173-183.

Hoppe, Uta C. et al, Minimally Invasive System for Baroreflex Activation Therapy Chronically Lowers Blood Pressure with Pacemaker-like Safety Profile: Results from the Barostim Neo Ttrial, J Am Soc Hypertens. Jul.-Aug. 2012;6 (4):270-6.

Howard, James P. et al, Size of Blood Pressure Reduction from Renal Denervation: Insights from Meta-Analysis of Antihypertensive Drug Trials of 4121 Patients with Focus on Trial Design: the CONVERGE Report, Heart 2013;0:1-9.

Howard, James P. et al, Unintentional Overestimation of an Expected Antihypertensive Effect in Drug and Device Trials: Mechanisms and Solutions, International Journal of Cardiology, vol. 172, Issue 1, Mar. 1, 2014, pp. 29-35.

Howell, Marcus H. et al, Tandem Stenting of Crossed Renal Arteries with Ostial Stenosis, Tex Heart Inst J. 2000; 27(2): 166-169.

Hoye, Neil A. et al, Endovascular Renal Denervation: A Novel Sympatholytic with Relevance to Chronic Kidney Disease, Clinical Kidney Journal Advance Access, (2013) 0: 1-8.

(56) References Cited

OTHER PUBLICATIONS

Huang, Shoei K. Stephen et al, Radiofrequency Catheter Ablation of Cardiac Arrhythmias, Basic Concepts and Clinical Applications, Wiley-Blackwell, Jun. 2000, 1-12.

Huang, Wann-Chu, Renal Denervation Prevents and Reverses Hyperinsulinemia-Induced Hypertension in Rats, Hypertension Journal of The American Heart Association, 1998;32:249-254.

Humpreys, Michael H., Renal Nerves and CKD: Is Renal Denervation the Answer?, Journal of The American Socity of Nephrology, 2012, 23: 1-3.

Irigoyen, M.C.C. et al, Baroreflex Control of Sympathetic Activity in Experimental Hypertension, Brazilian Journal of Medical and Biological Research, (1998) 31: 1213-1220.

Izzo, Jr, Joseph L. et al, The Sympathetic Nervous System and Baroreflexes in Hypertension and Hypotension, Current Hypertension Reports 1999, 3:254-263.

Jackman, Warren M. et al, Catheter Ablation of Arrhythmias, Proposed Anatomy and Catheter Ablation of Epicardial Posteroseptal and Left Posterior Accessory AV Pathways (Chapter 16), 2002, Futura Publishing Company, Inc., 321-343.

Jaff, Michael R. et al, Kidney Stenting Lowers Blood Pressure in Patients with Severe Hypertension; Catheterization and Cardiovascular Interventions; Published Online: Jun. 27, 2012 (DOI: 10.1002/ccd24449); Print Issue Date: Sep. 2012. URL: http://onlinelibrary.wiley.com/doi/10.1002l ccd.24449/abstract.

Jain, Mudit K. et al, A Three-Dimensional Finite Element Model of Radiofrequency Ablation with Blood Flow and Its Experimental Validation, Annals of Biomedical Engineering, vol. 28, pp. 1075-1084, 2000.

Jais, Pierre et al, Efficacy and Safety of Septal and Left-Atrial Linear Ablation for Atrial Fibrillation, The American Journal of Cardiology, vol. 84 (9A), Nov. 1999, 139R-146R.

Janssen, Ben J.A. et al, Frequency-Dependent Modulation of Renal Blood Flow by Renal Nerve Activity in Conscious Rabbits, American Journal of Physiology, 1997, 273:R597-R608.

Janssen, Ben J.A. et al, Renal Nerves in Hypertension, Miner Electrolyte Metab 1989;15:74-82.

Jin, Yu et al, No Support for Renal Denervation in a Meta-Analysis, JACC vol. 62, No. 21, 2013 Correspondence Nov. 19-26, 2013:2029-30.

Kaltenbach, Benjamin et al, Renal Artery Stenosis After Renal Sympathetic Denervation, J Am Coll Cardiol. Dec. 25, 2012;60(25):2694-5.

Kaltenbach, Benjamin et al, Renal Sympathetic Denervation as Second-Line Therapy in Mild Resistant Hypertension: A Pilot Study, Catheterization and Cardiovascular Interventions 81:335-339 (2013).

Kamiya, Atsunori et al, Parallel Resetting of Arterial Baroreflex Control of Renal and Cardiac Sympathetic Nerve Activities During Upright Tilt in Rabbits, Am J Physiol Heart Circ Physiol 298: H1966-H1975, 2010.

Kandzari, David E. et al, Catheter-Based Renal Denervation for Resistant Hypertension: Rationale and Design of the Symplicity HTN-3 Trial, Clin. Cardiol. 35, 9, 528-535 (2012).

Kapural, Leonardo et al, Radiofrequency Ablation for Chronic Pain Control, Current Pain and Headache Reports 2001, 5:517-525.

Kassab, Salah et al, Renal Denervation Attenuates the Sodium Retention and Hypertension Associated with Obesity, Hypertension vol. 25, No. 4, Part 2 Apr. 1995.

Katholi, Richard E. et al, Decrease in Peripheral Sympathetic Nervous System Activity following Renal Denervation or Unclipping in the One-Kidney One-Clip Goldblatt Hypertensive Rat, The Journal of Clinical Investigation, Jan. 1982;69(1):55-62.

Katholi, Richard E. et al, Role of the Renal Nerves in the Pathogenesis of One-Kidney Renal Hypertension in the Rat, Hypertension. 1981;3:404-409.

Katholi, Richard E. et al, The Role of Renal Sympathetic Nerves in Hypertension: Has Percutaneous Renal Denervation Refocused Attention on Their Clinical Significance?; Progress in Cardiovascular Disease 52 (2009) 243-248.

Katritsis, Demosthenes et al, Recurrence of Left Atrium-Pulmonary Vein Conduction Following Successful Disconnection in Asymptomatic Patients, Europace (2004) 6, 425e432.

Killip III, Thomas, Oscillation of Blood Flow and Vascular Resistance During Mayer Waves, Circulation Research, vol. XI, Dec. 1962, 987-993.

Kingwell, Bronwyn A. et al, Assessment of Gain of Tachycardia and Bradycardia Responses of Cardiac Baroreflex, Am J Physiol Heart Circ Physiol 260:H1254-H1263, 1991.

Kirchheim, H. et al, Sympathetic Modulation of Renal Hemodynamics, Renin Release and Sodium Excretion, Klin Wochenschr (1989) 67: 858-864.

Klein, GE et al, Endovascular Treatment of Renal Artery Aneurysms with Conventional Non-Detachable Microcoils and Guglielmi Detachable Coils, Br J Urol. Jun. 1997; 79(6):852-860.

Knight, Eric L. et al, Predictors of Decreased Renal Function in Patients with Heart Failure During Angiotensin-Converting Enzyme Inhibitor Therapy: Results from the Studies of Left Ventricular Dysfunction (SOLVD), American Heart Journal, vol. 138, No. 5, Part 1, Nov. 1999, 849-855.

Koepke, John P. et al, Functions of the Renal Nerves, The Physiologist, vol. 28, No. 1, Feb. 1985, 47-52.

Kompanowska-Jezierska, Elzbieta et al, Early Effects of Renal Denervation in the Anaesthetised Rat: Natriuresis and Increased Cortical Blood Flow, Journal of Physiology (2001), 531.2, pp. 527-534.

Krum, Henry et al, Catheter-Based Renal Sympathetic Denervation for Resistant Hypertension: A Multicentre Safety and Proof-of-Principle Cohort Study, www.thelancet.com vol. 373 Apr. 11, 2009 1275-1281.

Krum, Henry et al, Device-Based Antihypertensive Therapy: Therapeutic Modulation of the Autonomic Nervous System, Circulation. 2011;123:209-215.

La Grange, Ronald G. et al, Selective Stimulation of Renal Nerves in the Anesthetized Dog: Effect on Renin Release During Controlled Changes in Renal Hemodynamics, Circulation Research, Journal of The American Heart Association, 1973;33:704-712.

Labeit, Alexander Michael et al, Changes in the Prevalence, Treatment and Control of Hypertension in Germany? A Clinical-Epidemiological Study of 50.000 Primary Care Patients, PLOS ONE, Dec. 2012, vol. 7, Issue 12, e52229, 1-11.

Labonte, Sylvain, Numerical Model for Radio-Frequency Ablation of the Endocardium and its Experimental Validation, IEEE Transactions on Biomedical Engineering, vol. 41, No. 2. February 1994, 108-115.

Lambert, Gavin W. et al, Health-Related Quality of Life After Renal Denervation in Patients With Treatment-Resistant Hypertension, Hypertension. 2012;60:1479-1484.

Lee, Sang Joon et al, Ultrasonic Energy in Endoscopic Surgery, Yonsei Medical Journal, vol. 40, No. 6, pp. 545-549, 1999.

Leertouwer, Trude C. et al, In-Vitro Validation, with Histology, of Intravascular Ultrasound in Renal Arteries, Journal of Hypertension 1999, vol. 17 No. 2, 271-277.

Leishman, A.W.D., Hypertension—Treated and Untreated, British Medical Journal, May 1959, 1361-1368.

Leonard, Bridget L. et al, Differential Regulation of the Oscillations in Sympathetic Nerve Activity and Renal Blood Flow Following Volume Expansion, Autonomic Neuroscience: Basic and Clinical 83 (2000) 19-28.

Levin, Stephen, Ardian: Succeeding Where Drugs Fail Treating Hypertension in the Cath Lab, In Vivo: The Business & Medicine Report, vol. 27, No. 10, Nov. 2009.

Litynski, Grzegorz S., Kurt Semm and the Fight against Skepticism: Endoscopic Hemostasis, Laparoscopic Appendectomy, and Semm's Impact on the "Laparoscopic Revolution", JSLS. Jul.-Sep. 1998; 2(3): 309-313.

Lu, David S.K. et al, Effect of Vessel Size on Creation of Hepatic Radiofrequency Lesions in Pigs: Assessment of the "Heat Sink" Effect, American Journal of Radiology, 178, Jan. 2002, 47-51.

Luscher, Thomas F. et al, Renal Nerve Ablation After SYMPLICITY HTN-3: Confused at the Higher Level?; European Heart Journal, doi:10.1093/eurheartj/ehu195; May 14, 2014.

(56) References Cited

OTHER PUBLICATIONS

Lustgarten, Daniel L. et al, Cryothermal Ablation: Mechanism of Tissue Injury and Current Experience in the Treatment of Tachyarrhythmias, Progress in Cardiovascular Diseases, vol. 41, No. 6 May/Jun. 1999: pp. 481-498.

Mahfoud, Felix et al, Expert Consensus Document from the European Society of Cardiology on Catheter-Based Renal Denervation, European Heart Journal, Jul. 2013;34(28):2149-57.

Mancia, Giuseppe et al, Sympathetic Activation in the Pathogenesis of Hypertension and Progression of Organ Damage, Hypertension Journal of The American Heart Association, 1999, 34:724-728.

McGahan, John P. et al, History of Ablation, Tumor Ablation, 2005, pp. 3-16.

Medtronic, Inc., J.P. Morgan Healthcare Conference, Corrected Transcript, Jan. 13, 2014, Factset:Callstreet, www.callstreet.com.

Medtronic, Inc., Medtronic Announces U.S. Renal Denervation Pivotal Trial Fails to Meet Primary Efficacy Endpoint While Meeting Primary Safety Endpoint, www.medtronic.com, Jan. 9, 2014.

Medtronic, Inc., RDN Therapy with the Symplicity Renal Denervation System, Procedure Fact Sheet, www.medtronic.com, 2011.

Medtronic, Inc., Renal Denervation (RDN) Novel Catheter-based Treatment for Hypertension, Symplicity RDN System Common Q&A, 2011.

Medtronic, Inc., Scientific Basis Behind Renal Denervation for the Control of Hypertension, Dec. 2012, http://www.icimeeting.com/2012/images/stories/PDF/1448_Wilcox_I_Mon.pdf.

Mehdirad, Ali et al, Temperature Controlled RF Ablation in Canine Ventricle and Coronary Sinus using 7 Fr or 5 Fr Ablation Electrodes, PACE, vol. 21, Jan. 1998, Part II, 316-321.

Meredith, I T et al, Exercise Training Lowers Resting Renal But Not Cardiac Sympathetic Activity in Humans; Hypertension Journal of The American Heart Association, 1991;18:575-582.

Michaelis, Lawrence L. et al, Effects of Renal Denervation and Renin Depletion on the Renal Responses to Intravascular Volume Expansion, Ann Surg. Mar. 1972; 175(3): 424-430.

Millard, F.C. et al, Renal Embolization for Ablation of Function in Renal Failure and Hypertension, Postgraduate Medical Journal (1989) 65,729-734.

Moak, Jeffrey P. et al, Case Report: Pulmonary Vein Stenosis Following RF Ablation of Paroxysmal Atrial Fibrillation: Successful Treatment with Balloon Dilation, Journal of Interventional Cardiac Electrophysiology, Dec. 2000, 4, 4:621-631.

Mogil, Robert A. et al, Renal Innervation and Renin Activity in Salt Metabolism and Hypertension, American Journal of Physiology, vol. 216, No. 4, Apr. 1969, 693-697.

Morita, Hironobu et al, Neural Control of Urinary Sodium Excretion During Hypertonic NaCl Load in Conscious Rabbits: Role of Renal and Hepatic Nerves and Baroreceptors, Journal of the Autonomic Nervous System, 34 (1991).

Morrissey, D.M. et al, Sympathectomy in the Treatment of Hypertension, The Lancet, Feb. 1953, 403-408.

Mortara, Andrea et al, Nonselective Beta-Adrenergic Blocking Agent, Carvedilol, Improves Arterial Baroflex Gain and Heart Rate Variability in Patients With Stable Chronic Heart Failure, Journal of the American College of Cardiology, vol. 36, No. 5, 2000, 1612-1618.

Moss, Jonathan, Interventional Radiology and Renal Denervation, Interventions, vol. 13, Issue 3, 2013.

Naghavi, Morteza et al, Thermography Basket Catheter: In Vivo Measurement of the Temperature of Atherosclerotic Plaques for Detection of Vulnerable Plaques, Catheterization and Cardiovascular Interventions 59:52-59 (2003).

Naidoo, N. et al, Thoracic Splanchnic Nerves: Implications for Splanchnic Denervation, Journal of Anatomy, Nov. 2001;199(Pt 5):585-590.

Nakagawa, A. et al, Selective Ablation of Porcine and Rabbit Liver Tissue Using Radiofrequency: Preclinical Study, European Surgical Research, 1999;31:371-379.

Nakagawa, Hiroshi et al, Inverse Relationship Between Electrode Size and Lesion Size During Radiofrequency Ablation With Active Electrode Cooling, Circulation. Aug. 4, 1998;98(5):458-465.

Nanni, Gregg S. et al, Control of Hypertension by Ethanol Renal Ablation, Radiology 148: 51-54, Jul. 1983.

Ndegwa, S., Catheter-Based Renal Denervation for Treatment-Resistant Hypertension [Issues in emerging health technologies issue 121]. Ottawa: Canadian Agency for Drugs and Technologies in Health; 2013.

Neutel, Joel M., Hypertension and Its Management: A Problem in Need of New Treatment Strategies, Journal of Renin-Angiotensin-Aldosterone System 2000 1: S10-S13.

Newcombe, C.P. et al, Sympathectomy for Hypertension, British Medical Journal, Jan. 1959, 142-144.

Ng, Fu Siong et al, Catheter Ablation of Atrial Fibrillation, Clinical Cardiology, 25, 384-394 (2002).

Norman, Roger A. et al, Role of the Renal Nerves in One-Kidney, One Clip Hypertension in Rats, Hypertension Journal of The American Heart Association, 1984;6:622-626.

Nozawa, Takashi et al, Effects of Long-Term Renal Sympathetic Denervation on Heart Failure After Myocardial Infarction in Rats, Heart Vessels (2002) 16:51-56.

O'Connor, Brian K. et al, Radiofrequency Ablation of a Posteroseptal Accessory Pathway Via the Middle Cardiac Vein in a Six-Year-Old Child, PACE, vol. 20, Oct. 1997, Part 1, 2504-2507.

O'Hagen, Kathleen P. et al, Renal Denervation Decreases Blood Pressure in DOCA-Treated Miniature Swine With Established Hypertension, American Journal of Hypertension, 1990; 3:62-64.

Oliveira, Vera L.L. et al, Renal Denervation Normalizes Pressure and Baroreceptor Reflex in High Renin Hypertension in Conscious Rats, Hypertension vol. 19, No. 2 Feb. 1992, Supplement II, II-17-II-21.

Omran, Heyder et al, Echocardiographic Imaging of Coronary Sinus Diverticula and Middle Cardiac Veins in Patients with Preexcitation Syndrome: Impact—on Radiofrequency Catheter Ablation of Posteroseptal Accessory Pathways, Pace, vol. 18, Jun. 1995, 1236-1243.

Oparil, Suzanne et al, Renal Nerve Ablation: Emerging Role in Therapeutics; Blood Pressure, Oct. 2011, vol. 20, No. 5 , pp. 253-255.

Oral, Hakan et al, Pulmonary Vein Isolation for Paroxysmal and Persistent Atrial Fibrillation, Circulation Journal of The American Heart Association, 2002;105:1077-1081.

Osborn, Jeffrey L. et al, Long-Term Increases in Renal Sympathetic Nerve Activity and Hypertension, Clinical and Experimental Pharmacology and Physiology (1997) 24,72-76.

Osborn, John W., The Sympathetic Nervous System and Long-Term Regulation of Arterial Pressure: What Are the Critical Questions?, Clinical and Experimental Pharmacology and Physiology (1997) 24, 68-71.

Ou, Baiqing et al, Baroreflex Sensitivity Predicts the Induction of Ventricular Arrhythmias by Cesium Chloride in Rabbits, Japanese Circulation Journal, 1999; 63: 783-788.

Oz, Mehmet, Pressure Relief, TIME Magazine, Monday, Jan. 9, 2012.

Page, Irvine H. et al, Mechanisms, Diagnosis and Treatment of Hypertension of Renal Vascular Origin, Annals of Internal Medicine, Aug. 1959, vol. 51, No. 2, 196-211.

Page, Irvine H. et al, Mechanisms, Diagnosis and Treatment of Hypertension of Renal Vascular Origin; Annals of Internal Medicine, Aug. 1959;51:196-211.

Page, Irvine H. et al, The Effect of Renal Denervation on the Level of Arterial Blood Pressure and Renal Function in Essential Hypertension, Journal of Clinical Investigation, 1935;14(1):27-30.

Page, Irvine H. et al, The Effects of Renal Denervation on Patients Suffering from Nephritis, J Clin Invest. 1935;14 (4):443-458.

Page, Irvine H., The Effect of Renal Efficiency of Lowering Arterial Blood Pressure in Cases of Essential Hypertension and Nephritis, Journal of Clinical Investigation, Nov. 1934; 13(6): 909-915.

Page, Max, Section of Surgery, Discussion on the Surgical Treatment of Hypertension, Proceedings of the Royal Society of Medicine, vol. XLI, Feb. 1948, 359-372.

Papademetriou, Vasilios, Hypertension and the Simplicity Renal Denervation System, Scientific Background, www.medtronic.com, 2011.

(56) References Cited

OTHER PUBLICATIONS

Pappone, Carlo et al, Circumferential Radiofrequency Ablation of Pulmonary Vein Ostia: A New Anatomic Approach for Curing Atrial Fibrillation, Circulation, Journal of The American Heart Association, 2000;102:2619-2628.

Parati, Gianfranco et al, The Human Sympathetic Nervous System: Its Relevance in Hypertension and Heart Failure, European Heart Journal (2012) 33, 1058-1066.

Parmar, Arundhati, Analyst: Medtronic Will Likely Acquire Another Hypertension Therapy Firm, Medcity News, Apr. 27, 2012; 3:06 p.m.; medcitynews.com.

Pavlovich, Christian P. et al, Percutaneous Radio Requency Ablation of Small Renal Tumors: Initial Results; The Journal of Urology, vol. 167, Jan. 10-15, 2002.

Peet, Max Minor, Hypertension and Its Surgical Treatment by Bilateral Supradiaphragmatic Splanchnicectomy, American Journal of Surgery, vol. 75, Issue 1, Jan. 1948, 48-68.

Perry, C. Bruce, Malignant Hypertension Cured by Unilateral Nephrectomy, British Heart Journal, Jul. 1945; 7(3):139-142.

Persu, Alexandre et al, Renal Denervation: Ultima Ratio or Standard in Treatment-Resistant Hypertension, Hypertension Journal of The American Heart Association, Sep. 2012;60(3):596-606.

Peterson, Helen Hogh et al, Lesion Dimensions During Temperature-Controlled Radiofrequency Catheter Ablation of Left Ventricular Porcine Myocardium Impact of Ablation Site, Electrode Size, and Convective Cooling, Circulation Journal of The American Heart Association, 1999;99:319-325.

Plouin, Pierre-Francois et al, Blood Pressure Outcome of Angioplasty in Atherosclerotic Renal Artery Stenosis a Randomized Trial, Hypertension Journal of The American Heart Association, 1998;31:823-829.

Poutasse, Eugene F., Surgical Treatment of Renal Hypertension, American Journal of Surgery, vol. 107, Jan. 1964, 97-103.

Pugsley, M.K. et al, The Vascular System an Overview of Structure and Function, Journal of Pharmacological and Toxicological Methods 44 (2000) 333-340.

Putney, John Paul, Are Secondary Considerations Still "Secondary"?: An Examination of Objective Indicia of Nonobviousness Five Years After KSR, Intellectual Property Brief, vol. 4, Issue 2, Article 5, 2012, 45-59.

Ramsay, Lawrence E. et al, Blood Pressure Response to Percutaneous Transluminal Angioplasty for Renovascular Hypertension: An Overview of Published Series; British Medical Journal Mar. 3, 1990; 300(6724): 569-572.

Rippy, Marian K. et al, Catheter-Based Renal Sympathetic Denervation: Chronic Preclinical Evidence for Renal Artery Safety, Clin Res Cardiol (2011) 100:1095-1101.

Ritz, Eberhard, New Approaches to Pathogenesis and Management of Hypertension, Clin J Am Soc Nephrol 4: 1886-1891, 2009.

\* cited by examiner

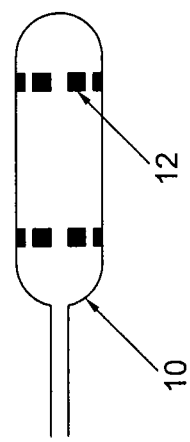
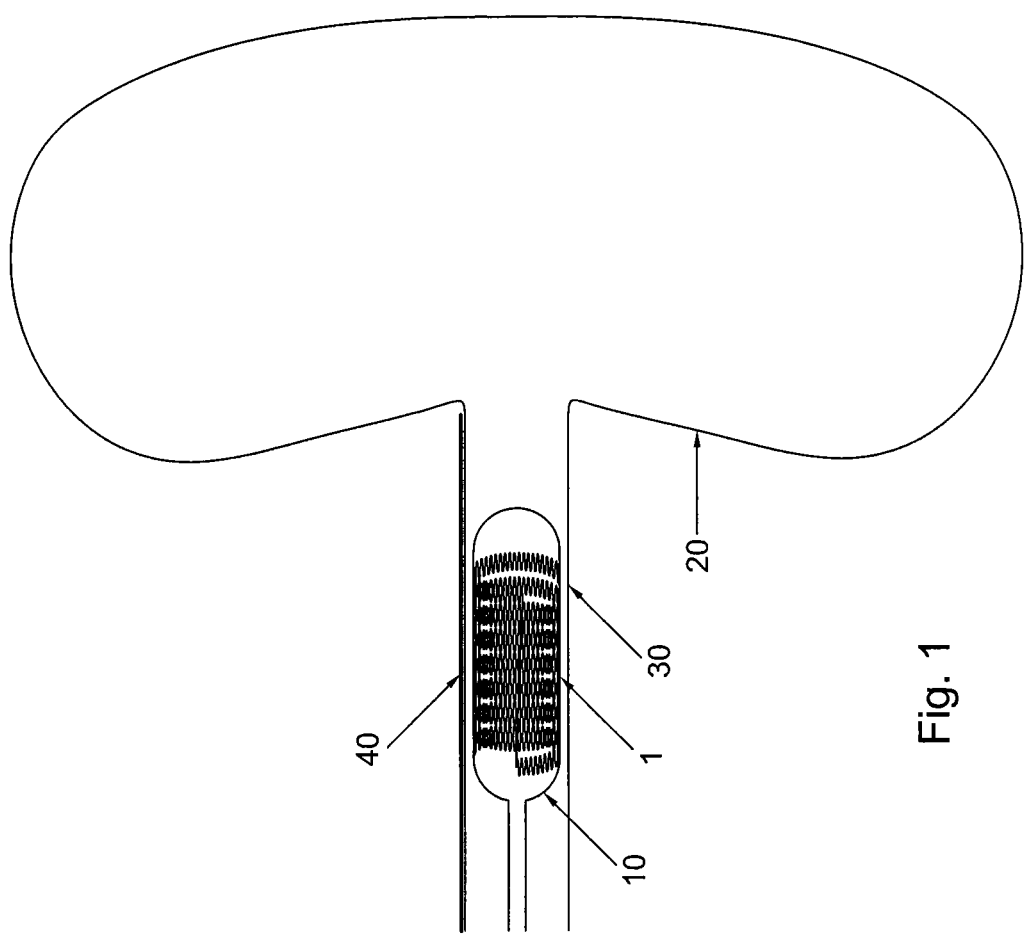

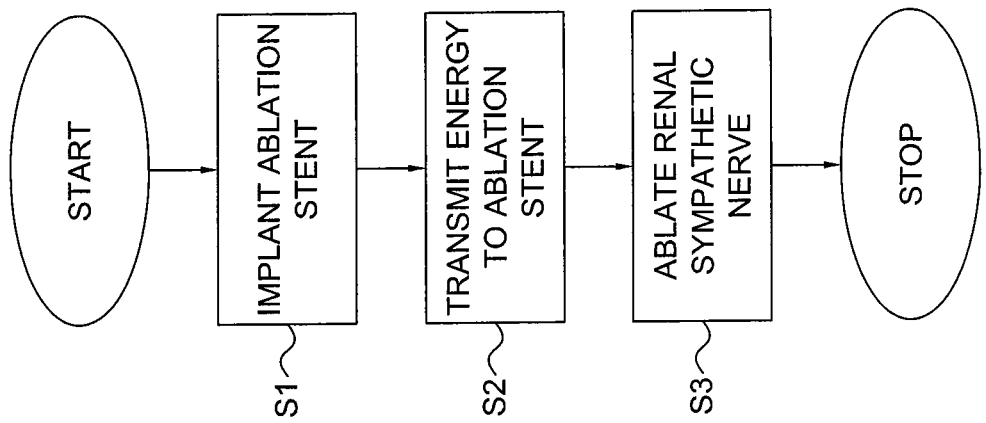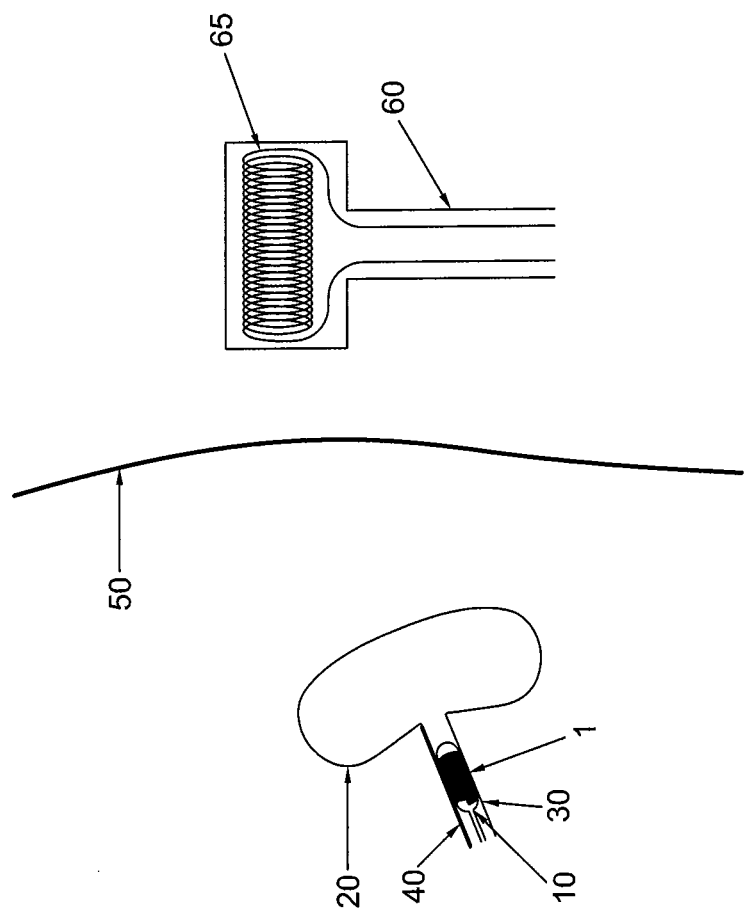

US 8,934,988 B2

ABLATION STENT WITH MEANDER STRUCTURE

TECHNICAL FIELD

The embodiments generally relate to an ablation stent and to a method of treating hypertension using such an ablation stent.

BACKGROUND

Hypertension is a chronic medical condition in which the blood pressure in the arteries is elevated. The high blood pressure implies that the heart of the patient needs to work harder than normal to maintain blood circulation throughout the body.

Persistent hypertension also has severe sequelae in the form of increased risk for stroke, myocardial infarction, heart failure, aortic aneurysm and chronic kidney disease.

A general approach in treating hypertension is a change of lifestyle, including dietary changes, physical exercise and weight loss. Medications in the form of antihypertensive drugs are also common, possible in the form of various combinations of different classes of antihypertensive agents, such as beta-blockers, calcium channel blockers (CCB), angiotensin converting enzyme inhibitors (ACE-I) and thiazide-based diuretic.

Another approach to combat hypertension is to use renal sympathetic nerve ablation, Schlaich et al., Renal sympathetic-nerve ablation for uncontrolled hypertension, *The New England Journal of Medicine* 361: 932-934, 2009 and Krum et al., Catheter-based renal sympathetic denervation for resistant hypertension: a multicentre safety and proof-of-concept study, *Lancet* 373: 1275-1281, 2009. The sympathetic nervous system plays an important role in circulatory and metabolic control and has been established as a major contributor to the development of hypertension since elevated sympathetic nerve activity initiates and sustains elevated blood pressure. Consequences of increased sympathetic activity to the kidneys include sodium and water retention, increased renin release and alteration of renal blood flow—effects that contribute to both acute and long-term blood pressure elevations. Hence, a catheter-based radio frequency (RF) ablation has been tested to excise renal nerves. RF ablation was applied to renal arteries using an ablation catheter with the beneficial effects of reduced renin activity, increased renal plasma flow and a progressive and sustained reduction in systemic blood pressure.

There is, though, a need for an improved control in the renal sympathetic nerve ablation procedure as compared to the prior art techniques requiring a manual maintenance of the ablation catheter in correct position, with the imminent risk of causing lesions at undesired parts of the renal artery and surrounding tissue.

SUMMARY

It is a general objective to provide a method of treating hypertension. It is another general objective to provide equipment that can be used in a method of treating hypertension. These and other objectives are met by embodiments disclosed herein.

An aspect of the embodiments defines a method of treating or inhibiting hypertension in a patient. The method comprises implanting an ablation stent in a renal artery of the patient. Energy is transmitted to the ablation stent. This transmitted energy induces heat development in the ablation stent. The induced heat causes ablation of a renal sympathetic nerve present on an outside of the portion of the renal artery in which the ablation stent is present. The renal sympathetic nerve ablation leads to a reduction in the patient's blood pressure and thereby a treatment of the hypertension.

Another aspect of the embodiments relates to an ablation stent in the form of an N-turn coil of an electrically conductive wire, where N is a positive number equal to or larger than one. The electrically conductive wire forms a meander structure. A first end of the electrically conductive wire is connected to a second end of the wire.

The ablation stent of the embodiments achieves a significantly higher control of the ablation process as compared to prior art procedures using an RF ablation catheter.

BRIEF DESCRIPTION OF THE DRAWINGS

The invention, together with further objects and advantages thereof, may best be understood by making reference to the following description taken together with the accompanying drawings, in which:

FIG. 1 is a schematic illustration of an ablation stent introduced by an inflation balloon catheter in a renal artery to enable renal sympathetic nerve ablation;

FIG. 4 is a flow diagram of a method of treating or inhibiting hypertension according to an embodiment;

FIG. 5 is a schematic illustration of an inflation balloon catheter that can be used to provide energy to an ablation stent according to an embodiment;

FIG. 6 illustrates how an external device can be used to provide energy to an ablation stent according to an embodiment.

DETAILED DESCRIPTION

Figure 2:
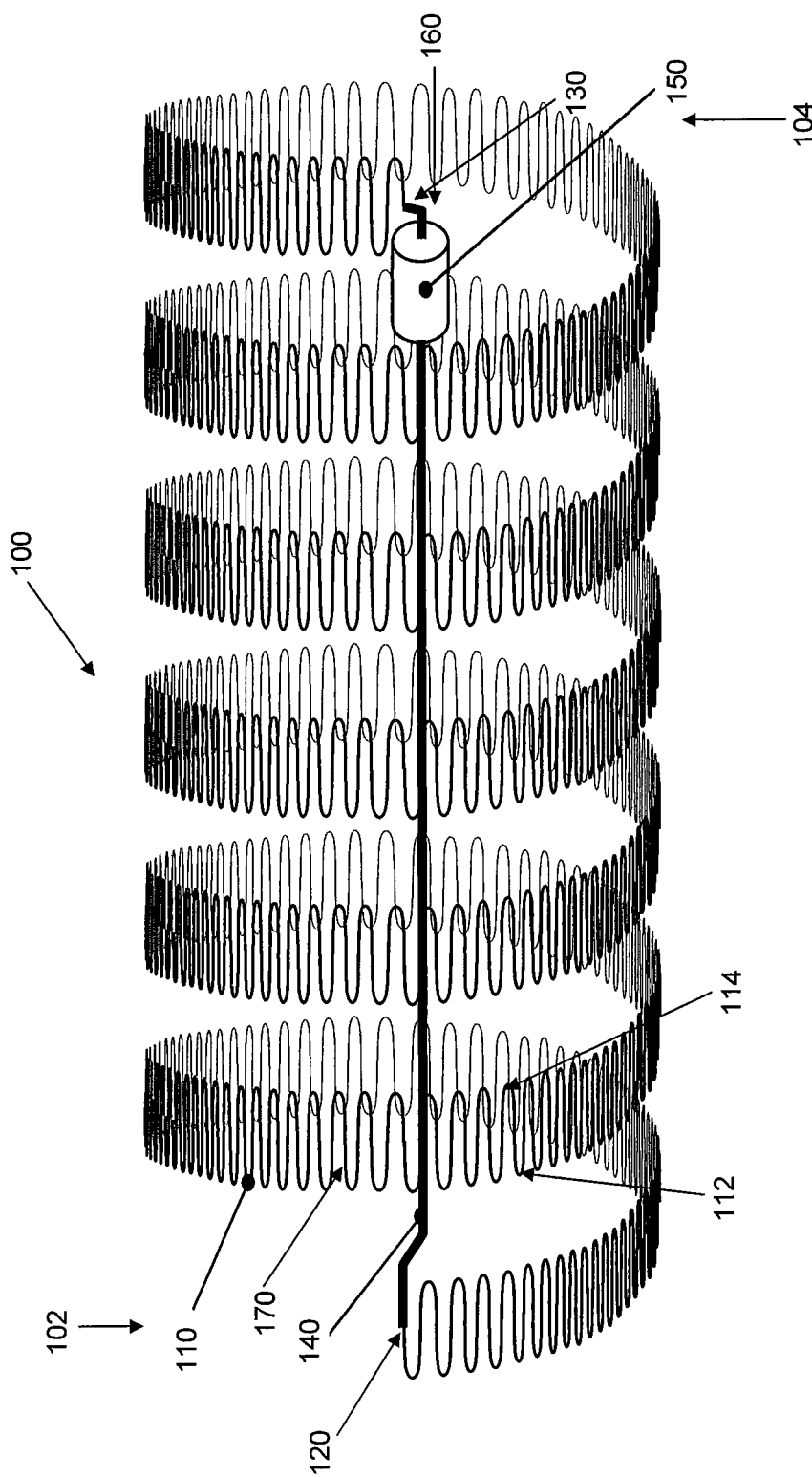
FIG. 2 is an illustration of an ablation stent according to an embodiment.

Throughout the drawings, the same reference numbers are used for similar or corresponding elements. The present embodiments generally relate to a method for treating or inhibiting hypertension and equipment used in such a method. In more detail, hypertension is treated through renal sympathetic nerve ablation, also referred to as renal sympathetic denervation in the art. In such a treatment approach, renal sympathetic nerves present on the outside of a renal artery, i.e. localized to the adventitia of the renal artery, are ablated. The denervation leads to reduced renin release, reduced sodium and water retention and improved renal blood flow, altogether causing a reduction in blood pressure of the patient.

The present embodiments in particular use a so-called ablation stent to effectuate the denervation and nerve ablation. Such an ablation stent is introduced into a renal artery of a kidney of a patient, preferably human patient, suffering from hypertension. The ablation stent is activated causing a local heating of the stent that ablates renal sympathetic nerves present on the outside of the portion of the renal artery where the ablation stent is arranged. FIG. 1 schematically illustrates this approach and shows a kidney 20 and a renal artery 30 of the kidney 20. In FIG. 1, a renal sympathetic nerve 40 is schematically indicated. An ablation stent 1 according to the embodiments is introduced into the renal artery 30 by an inflation balloon catheter 10, which is further disclosed herein.

According to an aspect of the embodiments an ablation stent is provided in the form of an N-turn coil of an electrically conductive wire. The number N is a positive number equal to or larger than one. Thus, the coil is either a single turn coil or a so-called multi-turn coil. The electrically conductive wire of the ablation stent forms a meander structure. Hence, the electrically conductive wire is running back and forth in a sinusoidal way. According to the embodiments, a first end of the electrically conductive wire is electrically connected to a second end of the electrically conductive wire to thereby form a closed circuit.

In a preferred embodiment the ablation stent forms a meander structure in each turn of the coil. It is, though, not necessary for achieving a desired compression and expansion effect of the ablation stent that the complete ablation stent forms a meander structure. For instance, the portions of the ablation stent in connection with the ends of the coil do not necessarily need to have a meander structure. These end portions could, for instance, have a decreasing diameter when traveling from the central coil portion towards respective end. The diameter at the ends could then be designed to basically correspond to the diameter of the central coil in the compressed state. Thus, once the ablation stent has been implanted into the correct site in the renal artery the central coil portion is, through the meander structure, allowed to expand from the compressed state into an expanded state with a diameter that is preferably at least equal to the inner diameter of the renal artery. The end portion of the ablation stent could then have a somewhat smaller diameter and therefore do not need any meander structure.

FIG. 2 is an illustration of an ablation stent 100 according to an embodiment in the form of a multiturn coil in which the electrically conductive wire 170 forms multiple turns 110. As is seen in FIG. 2, the electrically conductive wire 170 forms a meander structure, preferably in each turn 110 of the coil, and thereby has a sinusoidal shape forming the meander structure in each turn 110. The meander-shaped turns or periods enable the ablation stent 100 to radially expand from a compressed state in which the electrically conductive wire 170 in each turn or period of the meander structure is closely compressed to adjacent parts of the electrically conductive wire 170 in adjacent meander turns. FIG. 2 illustrates the ablation stent 100 in an expanded state where the electrically conductive wire 170 in one meander turn is spaced apart from adjacent parts of the electrically conductive wire 170 in adjacent meander turns. The ablation stent 100 can then be kept in the compressed state during implantation in the patient body when the ablation stent 100 is brought to the intended ablation site in a renal artery, see FIG. 1. At the ablation site the ablation stent 100 is allowed to radially expand to press onto the inner endothelial surface of the renal artery. In this expanded state the ablation stent 100 is safely kept immovable at the ablation site and there is basically no risk that the ablation stent 100 is unintentionally moved inside the renal artery.

In an embodiment that enables the radial expansion from a compressed state to an expanded state each crest 112 and each trough 114 of the sinusoidal shape of the meander structure faces one of a first end 102 of the coil or a second, opposite end 104 of the coil. Thus, the crests 112 and the troughs 114 are preferably aligned along the axial extension of the coil from the first end 102 to the second end 104. In such a case, each crest 112 preferably faces the first end 102 and each trough 114 preferably faces the second end 104.

The first end 120 of the electrically conductive wire 170 is electrically connected to the second end 130 of the electrically conductive wire 170. In an embodiment, these two ends 120, 130 are directly connected to each other to form a short circuit. In such a case, the first end 120 could be electrically connected to the second end 130 with an electrical conductor 140 running in a lumen 160 formed by the multi-turn helical coil.

In an embodiment, the electrical conductor 140 is provided with an electrically isolating coating around the electrical conductor 140. Such isolation around the electrical conductor 140 could be beneficial to prevent an unintentional short circuit between the electrical conductor 140 and the electrically conductive wire 170 in any of the turns of the ablation stent 100.

The ablation stent 100 preferably comprises a thermally-dependable conductive element 150 connected to the first end 120 and the second end 130 of the electrically conductive wire 170. The thermally-dependable conductive element 150 could then be arranged close to either of the ends 120, 130 or be present anywhere in the lumen 160 of the multi-turn helical coil. In FIG. 2 the thermally-dependable conductive element 150 is directly connected to the second end 130 and to the first end 120 via the electrical conductor 140. This should, however, merely be seen as an illustrative example. In other embodiments, the thermally-dependable conductive element 150 could be directly connected to the first end 120 and to the second end 130 via the electrical conductor 140 or be connected to the first end 120 with a first electrical conductor and to the second end 130 with a second electrical conductor. In this latter case, the electrical conductor 140 of FIG. 2 is basically divided into two parts of same or different lengths depending on where in the lumen 160 the thermally-dependable conductive element 150 is arranged.

The thermally-dependable conductive element 150 has an electrical conductance that is dependent on temperature. Thus, the conductance of the element 150 is a function of the temperature of the element 150. In a particular embodiment, the thermally-dependable conductive element 150 has a first electrical conductance at a first temperature and a second, lower electrical conductance at a second, higher temperature. This means that the conductance of the thermally-dependable conductive element 150 could be inversely proportional to the temperature. This temperature-dependency could be obtained in various ways. For instance, the conductance could decrease with increasing temperature in a continuous manner, such as linearly. Alternatively, the conductance could decrease step-by-step with increasing temperatures. It is also possible to have a significant or abrupt change in conductance at a given threshold temperature. Thus, below this temperature the thermally-dependable conductive element 150 has a first electrical conductance but above the threshold temperature the electrical conductance of the thermally-dependable conductive element 150 drops abruptly to a significantly lower value.

Denervation and renal sympathetic nerve ablation with the ablation stent 100 is, as is further discussed herein, performed by transmitting energy to the ablation stent inducing a current in the electrically conductive wire that in turn causes heat-development in the electrically conductive wire 170. It is this generated heat in the electrically conductive wire 170 that ablates the nerve on the outside of the renal artery.

The thermally-dependable conductive element 150 can then be used in order to get more control of the heat delivered to the surrounding tissue. The thermally-dependable conductive element 150 therefore prevents a too high increase in the temperature of the electrically conductive wire 170 that otherwise could cause unintentional damages to the renal artery and/or the blood flowing through the lumen 160 of the ablation stent 100. Hence, once the temperature in the electrically conductive wire 170 increases the electrical conductance of the thermally-dependable conductive element 150 drops thereby effectively restricting a current in the electrically conductive wire 170 and further heating of the electrically conductive wire 170. The thermally-dependable conductive element 150 effectively prevents too high heat development in the ablation stent 100 and thereby simplifies control of the heat inducement in the ablation stent 100.

The thermally-dependable conductive element 150 can be implemented according to various embodiments. In a first example, the thermally-dependable conductive element 150 is in the form of a thermal fuse configured to electrically disconnect the first end 120 of the electrically conductive wire 170 from the second end 130 of the electrically conductive wire 170 at a temperature exceeding a threshold temperature. This means that if the heat developed in the ablation stent 100 causes the temperature to rise above the threshold temperature, the thermal fuse will disconnect the two ends 120, 130 from each other, thereby effectively preventing further heat development and temperature rises in the electrically conductive wire 170.

The particular threshold temperature at which the thermal fuse disconnects the two ends 120, 130 from each other could be set to any temperature within an interval of from about 45° C. to about 85° C. Generally, ablation is typically conducted at a temperature of from about 40° C. to about 80° C., preferably from about 50° C. to about 80° C. The threshold temperature could then be set to minimize the risk of harming surrounding non-nervous tissue while still being able to achieve the desired ablation.

In a particular embodiment, the thermal fuse is a resettable thermal fuse that disconnects the two ends 120, 130 of the electrically conductive wire 170 if the temperature exceeds the threshold temperature and then electrically reconnects the two ends 120, 130 if the temperature drops below the threshold temperature. The thermal fuse then operates as a temperature-dependent electrical switch that is closed below the threshold temperature and is open above the threshold temperature.

There are several bimetal temperature switches and thermal bimetal switches available on the market that could be used as (resettable) thermal fuse according to the embodiments.

Another example of a thermally-dependable conductive element 150 according to the embodiments is a resistor with a positive temperature resistance coefficient having an electrical resistance that increases with increasing temperature. Such resistors are available on the market as PTC resistors. In operation, when the heat develops in the ablation stent 100 the resistance of the PTC resistor increases and thereby restricts the current that is induced in the electrically conductive wire 170. This effectively prevents further heat development in the ablation stent 100 and thereby an efficient control of the ablation process is achieved by reducing the risk for unintentional heat-based damages to surrounding tissue.

A further example of a thermally-dependable conductive element 150 that can be used in the ablation stent 100 is a temperature sensitive capacitor having a temperature-dependable capacitance. The temperature sensitive capacitor then forms a resonance circuit with the coil of the ablation stent 100 at a temperature below a threshold temperature. This resonance circuit is then tuned to an external circuitry used to induce a current in the electrically conductive wire, which is further disclosed herein. If the temperature increases beyond the threshold temperature, the coil and the temperature sensitive capacitor will be driven out of tune as the capacitance changes with the heat.

Figure 3:
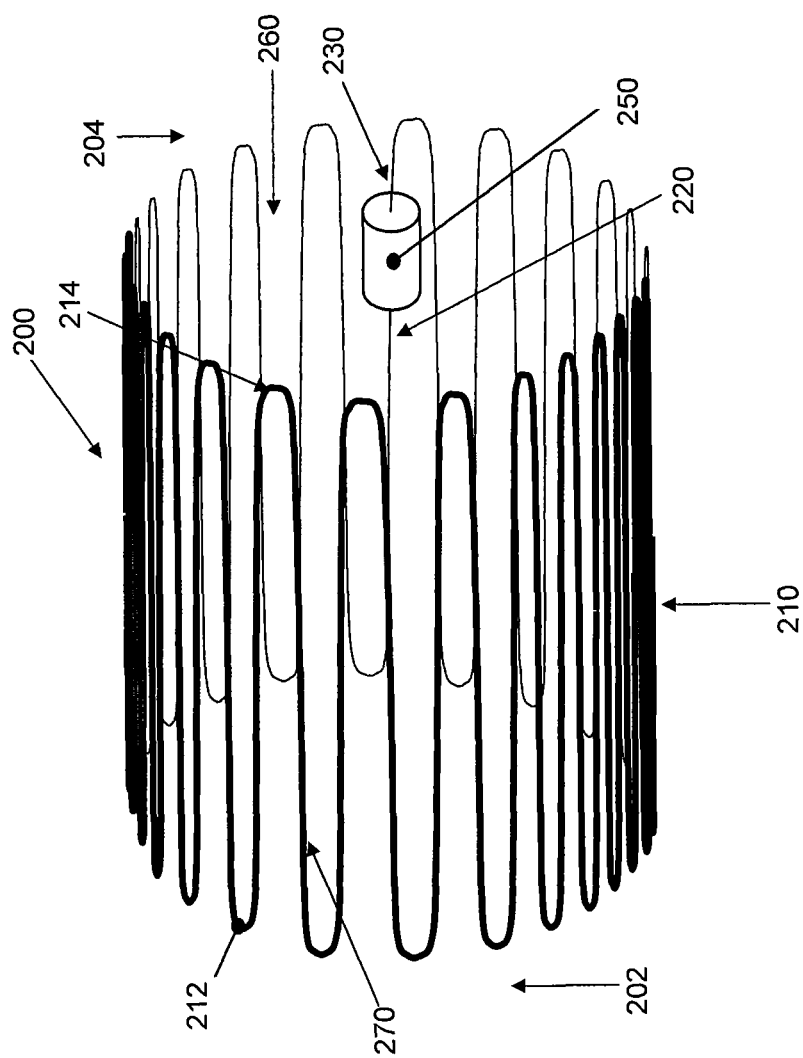
FIG. 3 is an illustration of an ablation stent according to another embodiment.

FIG. 3 is a schematic illustration of an ablation stent 200 according to another embodiment. In this embodiment, the ablation stent 200 is the form of a coil having a single turn 210 with the electrically conductive wire 270 forming a sinusoidal shape with a meander structure. As in FIG. 2, each crest 212 and trough 214, i.e. each turning point of the wire 270, preferably faces one of the first end 202 and the second end 204 of the coil. The ablation stent 200 can thereby be compressed into the compressed state and then expanded into the expanded state shown in FIG. 3. The electrically conductive wire 270 thereby expands close against the inner surface of the renal artery and allows blood to flow through the lumen 260 of the ablation stent 200.

The two ends 220, 230 of the electrically conductive wire 270 could be directly connected to each other or through a thermally-dependable conductive element 250.

The width or axial extension of the single-turn coil of FIG. 3 is preferably selected to match an ablation area in the renal artery. The same applies to the multi-turn coil of FIG. 2. This generally means that the axial extension of the single turn in FIG. 3 is preferably basically the same as the combined axial extension of the multiple turns in FIG. 2 if the two ablation stents 100, 200 are to match the same ablation area.

The electrically conductive wire can be manufactured in various electrically conductive materials. The material should furthermore be biocompatible and non-toxic. Hence, the material should not trigger any deleterious reactions when introduced into the patient body. A further characteristic of the material is that it should preferably have rather high resistance so that an induced current in the material will cause development of heat. Examples of suitable materials include stainless steel, MP35N (nickel-cobalt-chromium-molybdenum alloy) and titanium.

The above-presented examples of materials are all metallic materials that are not degradable in the patient body. Hence, the ablation stent is then preferably implanted at the target site in the renal artery to perform the denervation procedure and is then advantageously kept in place. Having the ablation stent implanted in the renal artery will generally not present any negative consequences to the patient. In fact, the ablation stent could have beneficial effects in terms of renal artery angioplasty to combat renal artery stenosis (RAS) and atherosclerosis. Such RAS is known to contribute to increased arterial hypertension and renal insufficiency. Thus, the ablation stent of these embodiments could have dual function of both ablating renal sympathetic nerves and achieving renal artery angioplasty.

In an alternative approach, the ablation stent and the electrically conductive wire could be made of an electrically conductive but biodegradable material. There are several different electrically conductive biodegradable polymers that could be used in these embodiments, including doped polypyrrole, conducting oligomers of pyrrole and thiophene, etc. The ablation stent will, in these embodiments, degrade in the patient body after the ablation procedure. Hence, the body will naturally decompose the ablation stent once the hypertension of the patient has been treated.

In an embodiment, the ablation stent can be provided with an isolating coating applied on at least a portion of the inner surface of the N-turn coil, preferably on the whole inner surface of the coil. This isolating coating is used to direct the heating developed in the electrically conductive wire radially outwards to the surrounding renal artery wall and the nerve network present around the renal artery. Hence, the isolating coating will thereby reduce the amount of heating reaching the lumen of the N-turn coil and the blood flowing through the ablation stent. This enables a more efficient ablation process by directing the developed heat to those areas where nerve ablation is desired while minimizing the amount of heat leaking to other areas where generally there is no need for any heating.

This concept of using an isolating coating can also be applied to a portion of the outer surface of the N-turn coil. For instance, there might be a need for performing nerve ablation at a restricted sector of the renal artery, i.e. not completely around the full circumference of the renal artery. As an example, a quarter, half or three quarters of the outer surface of the N-turn coil could be provided with the isolating coating to thereby restrict the nerve ablation to basically three quarters, half or a quarter of the circumference of the renal artery.

FIG. 4 is a flow diagram of a method of treating hypertension according to an embodiment using an ablation stent. The method comprises implanting an ablation stent in a renal artery of a patient in step S1. In a next step S2 energy is transmitted to the stent. This transmitted energy induces heat in the ablation stent that ablates, in step S3, a renal sympathetic nerve present on the outside of a portion of the renal artery comprising the ablation stent.

The ablation stent 1 is advantageously implanted in the renal artery 30 using a catheter, preferably an inflation balloon catheter 10. Introducing balloon-expandable stents in the renal artery are known in the art to combat atherosclerotic RAS. The ablation stent 1 of the embodiments can be implanted using similar techniques as these prior art anti-RAS stents. Schwarzwalder and Zeller, Renal artery stenting—developments in practice, *Interventional Cardiology* 4: 104-108, 2009 discloses a technique denoted the femoral approach where the renal artery is reached via the suprarenal aorta. Also techniques used in the art for introducing ablation catheters in the renal artery, such as disclosed in the articles by Schlaich et al. and Krum et al. mentioned in the background section, can be used to introduce the ablation stent 1 of the embodiments using an inflation balloon catheter 10.

In a typical embodiment, the ablation stent 1 of the embodiments is kept in a compressed state in or around the inflation balloon catheter 10 during implantation in the patient body. Once the intended target site is reached in the renal artery 30, as visually confirmed through X-ray or ultrasound imaging, the inflation balloon of the catheter is inflated causing expansion of the ablation stent 1 to the expanded state pressing against the inner vessel wall of the renal artery 30.

A patient most typically has two kidneys, each with at least one renal artery. In such a case, the implantation of an ablation stent in step S1 could be performed in one renal artery for one of the kidneys, or preferably a respective ablation stent is implanted in the renal arteries for both kidneys. Some humans have multiple renal arteries per kidney. In such a case, an ablation stent 1 could be implanted in one of these multiple renal arteries 30, i.e. preferably one ablation stent 1 for this kidney 20, or a respective ablation stent 1 could be implanted in each of the multiple renal arteries 30, i.e. multiple ablation stents 1 for this kidney 20.

The transmission of energy to the ablation stent 1 can be performed according to various embodiments depending on the design of the ablation stent. In an approach the ablation stent 1 is in the form of a multi-turn coil of an electrically conductive wire. The coil does not necessarily have to have a meander structure but advantageously has such a meander structure to facilitate compression and expansion of the coil.

In an embodiment of step S2, the ablation stent 1 is contacted with an electrode connected to a radio frequency (RF) generator. RF energy generated by the RF generator is then delivered to the ablation stent 1 through the electrode. The applied RF energy will cause a local heating of the electrically conductive wire of the ablation stent 1, where the developed heat will ablate surrounding renal sympathetic nerves to thereby cause a reduction in blood pressure.

In a particular embodiment as is shown in FIG. 5, the inflation balloon catheter 10 employed to carry the ablation stent 1 to the ablation site in the renal artery 30 and then expand the ablation stent 1 close to the inner wall of the renal artery 30 can comprise electrodes 12 that are used to deliver the RF energy to the ablation stent 1. The inflation balloon catheter 10 then comprises conductors running along the body of the catheter 10 to thereby interconnect the electrodes to the RF generator, which is kept outside of the patient body.

In this embodiment, transmission of energy to the ablation stent 1 is performed using equipment, such as an inflation balloon catheter with electrodes or a dedicated electrode-carrying catheter, in connection with implantation of the ablation stent 1. Thus, the energy-transmitting equipment needs to be present inside the patient body and connected to the ablation stent 1.

However, in an alternative embodiment the ablation stent 1 is designed as previously described herein in connection with FIG. 2 or 3. Thus, the ablation stent 1 is in the form of an N-turn coil of an electrically conductive wire, where N is a positive number equal to or larger than one. The electrically conductive wire forms a meander structure and a first end of the electrically conductive wire is electrically connected to a second end of the electrically conductive wire.

With such a design of the ablation stent 1 the transmission of energy to the ablation stent 1 in step S2 can be performed by generating an alternating magnetic flux substantially parallel to a longitudinal axis of the ablation stent 1. This alternating magnetic flux is thereby directed into the lumen defined by the ablation stent 1. The alternating magnetic flux will induce a current in the electrically conductive wire of the ablation stent 1 and thereby, due to the resistance of the electrically conductive wire, heat development, which causes ablation of renal sympathetic nerves 40 present in the vicinity to the ablation stent 1.

The alternating magnetic flux can be generated by a non-implantable magnetic flux generator 60 as is shown in FIG. 6. In this case, the non-implantable magnetic generator 60 comprises a coil 65 that is positioned on the outside of the patient body, such as behind the back 50 of the patient to generate the alternating magnetic flux in the ablation stent 1 positioned in the renal artery 30. Thus, in this approach the ablation stent 1 is heated using electromagnetic induction.

In this approach the implantation of the stent 1 in step S1 and the transmission of the energy in step S2 can be performed in two separate procedures. Thus, the ablation stent 1 is implanted and expanded in the renal artery 30 using the inflation balloon catheter 10. The catheter 10 is then removed leaving the ablation stent 1 at the desired ablation site. At this point or at any later point the magnetic flux generator 60 can be brought close to the patient body to generate the alternating magnetic flux that causes a heating of the ablation stent 1 and denervation of the renal sympathetic nerve 40.

A significant advantage with this approach is that ablation can be performed in multiple steps at different ablation occasions. This enables a stabilization of the blood pressure of the patient between each ablation occasion and measurement of blood pressure to verify whether further denervation is needed or whether a sufficient reduction in blood pressure has already been achieved. Thus, in this approach the blood pressure of the patient is measured following ablation of the renal sympathetic nerve. If the measured blood pressure exceeds a target blood pressure and therefore still is too high, the patient visits his/her physician which uses the magnetic flux generator 60 to generate an alternating magnetic flux that induces a heating of the ablation stent 1. Thus, further denervation or re-ablation is achieved.

The multi-step ablating procedure enables use of a very mild heating at each ablation occasion to thereby minimize any tissue damage besides the denervation caused by the heating of the ablation stent 1. If the heating and denervation obtained at a first ablation occasion were not sufficient to cause a reduction in the blood pressure below the target blood pressure, a new ablation occasion can be performed. This procedure can in fact be repeated as many times as is required in order to cause sufficient denervation and blood pressure drop.

Figure 7:
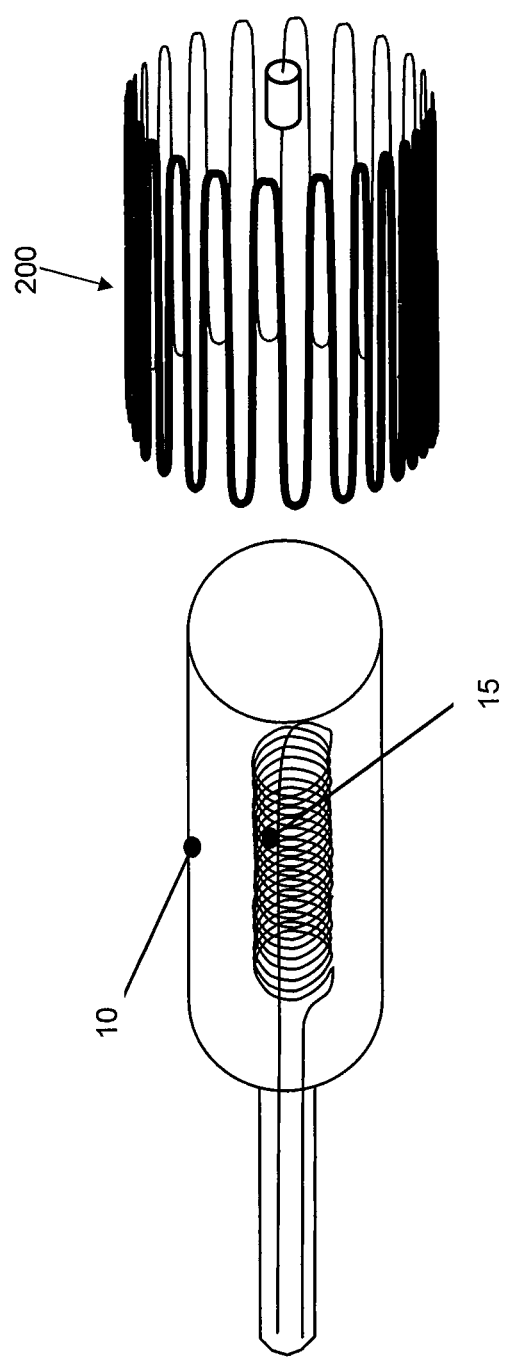
FIG. 7 illustrates how an inflation balloon catheter can be used to provide energy to an ablation stent according to an embodiment.

Applied alternating magnetic flux can also be used in an invasive approach by arranging a catheter having a coil of an electrically conductive material relative to the ablation stent so that an axis of said coil is aligned with, i.e. substantially parallel to, the longitudinal axis of the ablation stent. For instance, the catheter can be arranged to introduce the coil in the lumen of the ablation stent. An alternating current is then applied to this coil of the catheter to cause generation of the alternating magnetic flux that induces heating of the ablation stent. FIG. 7 illustrates an embodiment of this approach. In this case the inflation balloon catheter 10 comprises the coil 15 and is used, after inflation and expansion of the ablation stent 200, to generate the alternating magnetic flux.

The present embodiments provide significant advantages over the prior art renal denervation techniques that are based on the RF ablation catheters. In the prior art, the physician needs to manually keep the RF ablation catheter completely immovable during the whole ablation procedure. This is very hard and there is a significant risk that the RF ablation catheter is moved slightly during ablation thereby leading to inefficient nerve ablations and a risk of harming other tissues.

The present embodiments in clear contrast have an ablation stent that is implanted and immobilized at a target ablation site. When applying energy to the ablation stent the induced heating will reach the desired nerve site causing an efficient nerve ablation while minimizing harmful heating of other tissues.

A further advantage of some of the embodiments of the invention is that heat generation in the ablation stent can be induced by non-implantable devices in a non-invasive procedure that can be performed separate from the implantation of the ablation stent. It is furthermore possible in these embodiments to divide the ablation procedure in multiple steps with intermediate blood pressure verifications. This generally enables using a lower ablation stent heating and thereby reducing the risk of harming other tissue.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

What is claimed is:

1. An ablation stent comprising:
an N-turn coil of an electrically conductive wire, wherein N is a positive number equal to or larger than one, and wherein the electrically conductive wire forms a meander structure and a first end of the electrically conductive wire is electrically connected to a second end of the electrically conductive wire to form a closed path.

2. The ablation stent according to claim 1, wherein the electrically conductive wire has a sinusoidal shape forming the meander structure, each crest and each trough of the sinusoidal shape faces one of a first end of the coil or a second, opposite end of the coil.

3. The ablation stent according to claim 1, further comprising a thermally-dependable conductive element connected to the first end of the electrically conductive wire and to the second end of the electrically conductive wire, the thermally-dependable conductive element having an electrical conductance that is dependent on temperature with a first electrical conductance at a first temperature and a second, lower electrical conductance at a second, higher temperature.

4. The ablation stent according to claim 3, wherein the thermally-dependable conductive element is a thermal fuse configured to electrically disconnect the first end of the electrically conductive wire from the second end of the electrically conductive wire at a temperature exceeding a threshold temperature.

5. The ablation stent according to claim 4, wherein the thermal fuse is a resettable thermal fuse configured to electrically disconnect the first end of the electrically conductive wire from the second end of the electrically conductive wire at a temperature exceeding the threshold temperature and electrically reconnect the first end of the electrically conductive wire and the second end of the electrically conductive wire if the temperature drops below the threshold temperature.

6. The ablation stent according to claim 3, wherein the thermally-dependable conductive element is a resistor with a positive temperature resistance coefficient having an electrical resistance that increases with increasing temperature.

7. The ablation stent according to claim 3, wherein the thermally-dependable conductive element is a temperature sensitive capacitor having a temperature-dependable capacitance, and wherein the temperature sensitive capacitor forms a resonance circuit with the coil at a temperature below a threshold temperature.

8. The ablation stent according to claim 1, wherein the N-turn coil is a single turn coil having an axial extension selected to match an ablation area.

9. The ablation stent according to claim 1, wherein the N-turn coil is a multi-turn helical coil having a lumen, wherein the first end of the electrically conductive wire is electrically connected to the second end of the electrically conductive wire with an electrical conductor running in the lumen.

10. The ablation stent according to claim 9, wherein the electrical conductor is provided with an electrically isolating coating around the electrical conductor.

11. The ablation stent according to claim 1, further comprising an isolating coating provided on at least a portion of an inner surface of the coil.

12. The ablation stent according to claim 1, wherein the electrically conductive wire forms the meander structure in each turn of the coil.

* * * * *